(12) United States Patent
Hynes et al.

(10) Patent No.: US 8,410,139 B2
(45) Date of Patent: Apr. 2, 2013

(54) PRODRUGS OF A PIPERIDINYL DERIVATIVE AS MODULATORS OF CHEMOKINE RECEPTOR ACTIVITY

(75) Inventors: John Hynes, Washington Crossing, PA (US); Percy H. Carter, Princeton, NJ (US); Lyndon A. M. Cornelius, Jackson, NJ (US); T.G. Murali Dhar, Newtown, PA (US); John V. Duncia, Newtown, PA (US); Satheesh Nair, Kothanur (IN); Joseph B. Santella, Springfield, PA (US); Jayakumar S. Warrier, Bangalore (IN); Hong Wu, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 148 days.

(21) Appl. No.: 12/896,955

(22) Filed: Oct. 4, 2010

(65) Prior Publication Data

US 2011/0082113 A1    Apr. 7, 2011

Related U.S. Application Data

(60) Provisional application No. 61/249,270, filed on Oct. 7, 2009.

(51) Int. Cl.
*A61K 31/445* (2006.01)
*C07D 211/44* (2006.01)
(52) U.S. Cl. ........................ 514/327; 546/217
(58) Field of Classification Search .................. 514/327; 546/217
See application file for complete search history.

(56) References Cited

U.S. PATENT DOCUMENTS

| 7,601,844 B2 | 10/2009 | Carter et al. | |
| 2009/0326010 A1* | 12/2009 | Santella | 514/327 |

FOREIGN PATENT DOCUMENTS

| WO | WO 2007/092681 | 8/2007 |
| WO | WO 2009/015164 | 1/2009 |
| WO | WO 2009/015166 | 1/2009 |
| WO | WO 2009/158452 | 12/2009 |

OTHER PUBLICATIONS

Bundgaard "Design of prodrugs" p. 1-3 (1985).*
Hu "Progrugs: effective solutions . . . " IDrugs v.7(8) p. 736.-742 (2004).*
Patrick "An introduction . . . " p. 119-123 (1995).*
Taylor "Improved passive oral . . . " Adv. Drug. Del. Rev. v.19m p. 131-148 (1996).*
Carson, K.G. et al., "CCR1 Antagonists", Annual Reports in Medicinal Chemistry, vol. 39, pp. 149-158 (2004).
Carter, P.H., "Chemokine receptor antagonism as an approach to anti-inflammatory therapy: 'just right' or plain wrong?", Current Opinion in Chemical Biology, vol. 6, pp. 510-525 (2002).
Lee, S.C. et al., "Cutaneous Injection of Human Subjects with Macrophage Inflammatory Protein-1α Induces Significant Recruitment of Neutrophils and Monocytes", The Journal of Immunology, vol. 164, pp. 3392-3401 (2000).
Premack, B.A. et al., "Chemokine receptors: Gateways to inflammation and infection", Nature Medicine, vol. 2, No. 11, pp. 1174-1178 (1996).
Saunders, J. et al., "Opportunities for novel therapeutic agents acting at chemokine receptors", Drug Discovery Today, vol. 4, No. 2, pp. 80-92 (1999).
Trivedi, B.K. et al., Chapter 17: "Chemokines: Targets for Novel Therapeutics", Annual Reports in Medicinal Chemistry, vol. 35, pp. 191-200, Academic Press, publ. (2000).

* cited by examiner

*Primary Examiner* — Celia Chang
(74) *Attorney, Agent, or Firm* — Laurelee A. Duncan; Elliott Korsen; Hong Liu

(57) ABSTRACT

The present application describes prodrugs of the compound of formula (I):

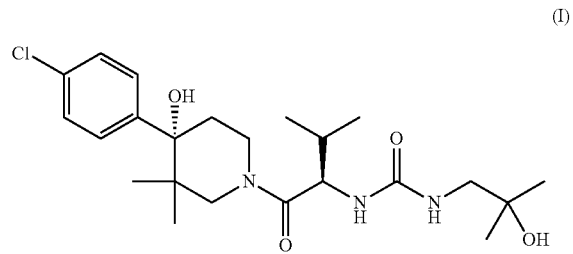

(I)

or stereoisomers or pharmaceutically acceptable salts thereof. In addition, methods of treating and preventing inflammatory diseases such as asthma and allergic diseases, as well as autoimmune pathologies such as rheumatoid arthritis using the prodrug compounds of the invention are disclosed.

4 Claims, No Drawings

PRODRUGS OF A PIPERIDINYL DERIVATIVE AS MODULATORS OF CHEMOKINE RECEPTOR ACTIVITY

RELATED APPLICATION

This application claims the benefit of U.S. Provisional Application No. 61/249,270, filed Oct. 7, 2009, incorporated herein by reference in its entirety.

FIELD OF THE INVENTION

This invention relates generally to prodrugs of a piperidinyl modulator of chemokine receptor activity, pharmaceutical compositions containing the same, and methods of using the same as an agent for treatment and prevention of inflammatory diseases, allergic and autoimmune diseases, and in particular, rheumatoid arthritis and transplant rejection.

BACKGROUND OF THE INVENTION

Chemokines are chemotactic cytokines, of molecular weight 6-15 kDa, that are released by a wide variety of cells to attract and activate, among other cell types, monocytes, macrophages, T and B lymphocytes, eosinophils, basophils and neutrophils. There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils.

The chemokines bind to specific cell-surface receptors belonging to the family of G-protein-coupled seven-transmembrane-domain proteins which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] CCR-2A and CCR-2B (or "CKR-2A"/"CKR-2B" or "CC-CKR-2A"/"CC-CKR-2B") [MCP-1, MCP-2, MCP-3, MCP-4, MCP-5]; CCR-3 (or "CKR-3" or "CC-CKR-3") [eotaxin-1, eotaxin-2, RANTES, MCP-3, MCP-4]; CCR-4 (or "CKR-4" or "CC-CKR-4") [TARC, MDC]; CCR-5 (or "CKR-5" OR "CC-CKR-5") [MIP-1α, RANTES, MIP-1β]; CCR-6 (or "CKR-6" or "CC-CKR-6") [LARC]; CCR-7 (or "CKR-7" or "CC-CKR-7") [ELC]; CCR-8 (or "CKR-8" or "CC-CKR-8") [1-309]; CCR-10 (or "CKR-10" or "CC-CKR-10") [MCP-1, MCP-3]; and CCR-11 [MCP-1, MCP-2, and MCP-4].

In addition to the mammalian chemokine receptors, mammalian cytomegaloviruses, herpesviruses and poxviruses have been shown to express, in infected cells, proteins with the binding properties of chemokine receptors. Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: Carter, P. H., Current Opinion in Chemical Biology 2002, 6, 510; Trivedi et al., Ann. Reports Med. Chem. 2000, 35, 191; Saunders et al., Drug Disc. Today 1999, 4, 80; Premack et al., Nature Medicine 1996, 2, 1174). For example, the chemokine macrophage inflammatory protein-1 (MIP-1α) and its receptor CC Chemokine Receptor 1 (CCR-1) play a pivotal role in attracting leukocytes to sites of inflammation and in subsequently activating these cells. When the chemokine MIP-1α binds to CCR-1, it induces a rapid increase in intracellular calcium concentration, increased expression of cellular adhesion molecules, cellular degranulation, and the promotion of leukocyte migration.

In addition, demonstration of the chemotactic properties of MIP-1α in humans has been provided experimentally. Human subjects, when injected intradermally with MIP-1α, experienced a rapid and significant influx of leukocytes to the site of injection (Brummet, M. E., J. Immun. 2000, 164, 3392-3401).

Demonstration of the importance of the MIP-1α/CCR-1 interaction has been provided by experiments with genetically modified mice. MIP-1α −/− mice had normal numbers of leukocytes, but were unable to recruit monocytes into sites of viral inflammation after immune challenge. Recently, MIP-1α −/− mice were shown to be resistant to collagen antibody induced arthritis. Likewise, CCR-1 −/− mice were unable to recruit neutrophils when challenged with MIP-1α in vivo; moreover, the peripheral blood neutrophils of CCR-1 null mice did not migrate in response to MIP-1α, thereby demonstrating the specificity of the MIP-1α/CCR-1 interaction. The viability and generally normal health of the MIP-1α −/− and CCR-1 −/− animals is noteworthy, in that disruption of the MIP-1α/CCR-1 interaction does not induce physiological crisis. Taken together, these data lead one to the conclusion that molecules that block the actions of MIP-1α would be useful in treating a number of inflammatory and autoimmune disorders. This hypothesis has now been validated in a number of different animal disease models, as described below.

It is known that MIP-1α is elevated in the synovial fluid and blood of patients with rheumatoid arthritis. Moreover, several studies have demonstrated the potential therapeutic value of antagonism of the MIP-1α/CCR1 interaction in treating rheumatoid arthritis.

It should also be noted that CCR-1 is also the receptor for the chemokines RANTES, MCP-3, HCC-1, Lkn-1/HCC-2, HCC-4, and MPIF-1 (Carter, P. H., Curr. Opin Chem. Bio. 2002, 6, 510-525). Since it is presumed that the new compound of formula (I) described herein antagonizes MIP-1α by binding to the CCR-1 receptor, it may be that this compound is also an effective antagonist of the actions of the aforementioned ligand that are mediated by CCR-1. Accordingly, when reference is made herein to "antagonism of MIP-1α," it is to be assumed that this is equivalent to "antagonism of chemokine stimulation of CCR-1."

Recently, a number of groups have described the development of small molecule antagonists of MIP-1α (reviewed in: Carson, K. G. et al., *Ann. Reports Med. Chem.* 2004, 39, 149-158).

SUMMARY OF THE INVENTION

Accordingly, the present invention provides prodrugs of an antagonist or partial agonist/antagonist of MIP-1α or CCR-1 receptor activity, or pharmaceutically acceptable salts thereof.

The present invention provides pharmaceutical compositions comprising a pharmaceutically acceptable carrier and a therapeutically effective amount of the prodrugs of the compound of the present invention or a pharmaceutically acceptable salt form thereof.

The present invention provides a method for treating rheumatoid arthritis and transplant rejection, comprising administering to a patient in need of such treatment a therapeutically effective amount of one or more of the prodrugs of the compound of the present invention or a pharmaceutically acceptable salt form thereof.

The present invention provides a method for treating inflammatory diseases, comprising administering to a patient in need of such treatment a therapeutically effective amount of one or more of the prodrugs of the compound of the present invention or a pharmaceutically acceptable salt form thereof.

The present invention provides prodrugs of a piperidinyl derivative for use in therapy.

The present invention provides the use of prodrugs of a piperidinyl derivative for the manufacture of a medicament for the treatment of inflammatory diseases.

DETAILED DESCRIPTION OF THE INVENTION

In one embodiment, the present invention provides prodrugs of a novel compound of formula (I):

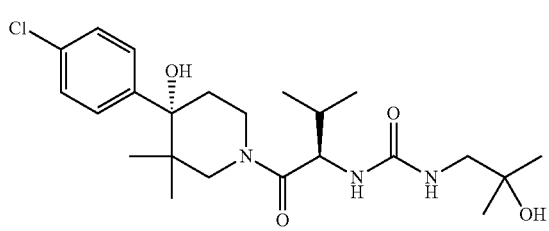

(I)

or stereoisomers or pharmaceutically acceptable salts thereof.

The present invention provides prodrugs of a piperidinyl compound that has an unexpectedly advantageous profile as compared to known inhibitors of CCR-1 activity, for example, the piperidinyl derivatives described in application US2007/0208056 A1, published Sep. 6, 2007, and assigned to applicant.

These prodrugs were prepared to provide compounds with improved permeability, solubility and/or stability for purposes of drug formulation and storage.

These prodrugs or pharmaceutically acceptable salts thereof have the following structures:

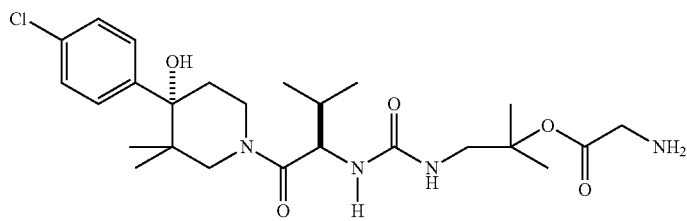

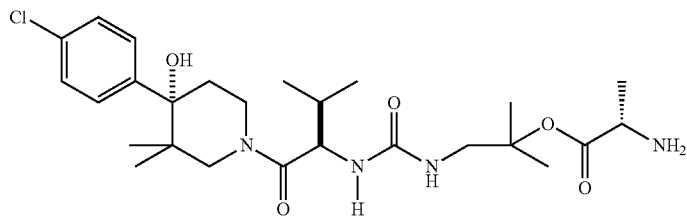

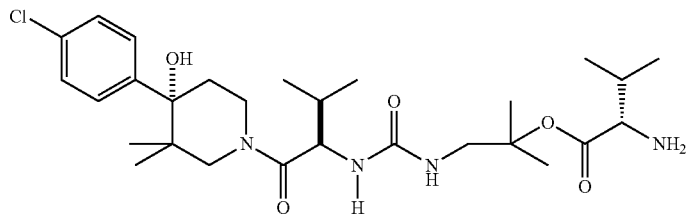

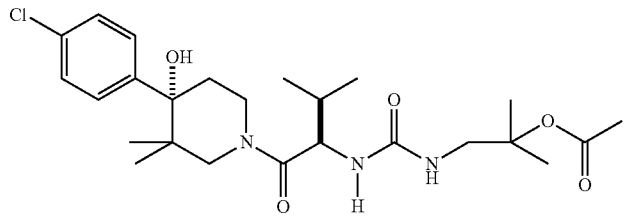

-continued
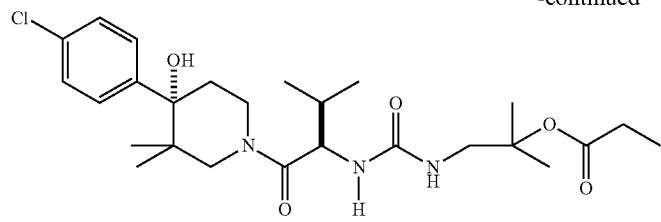
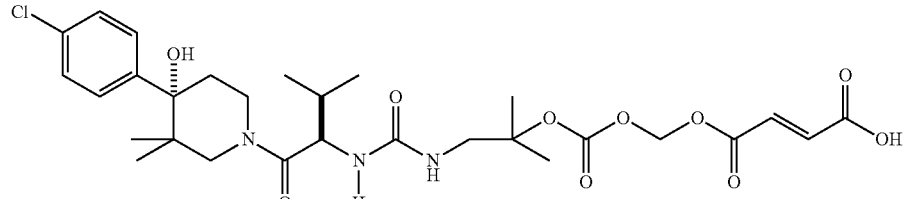
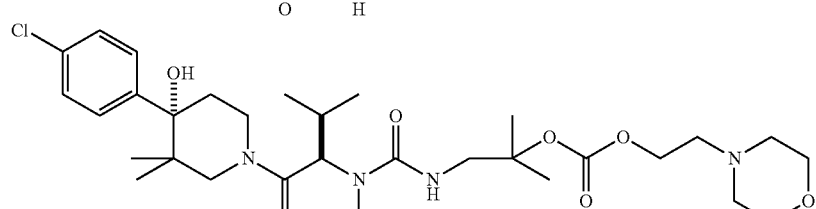
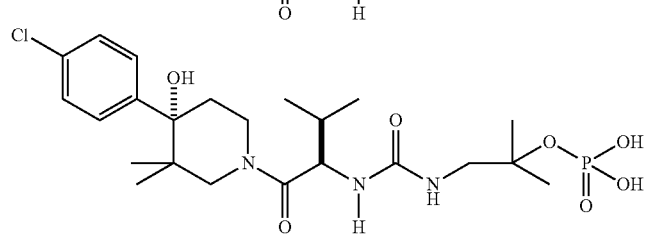
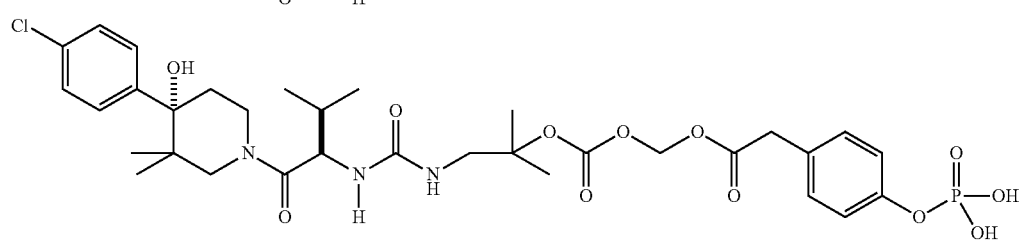
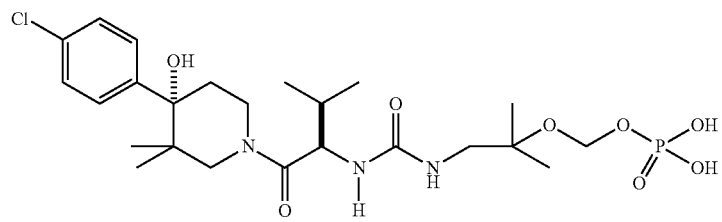
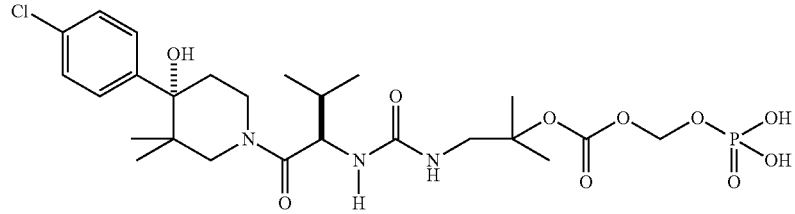
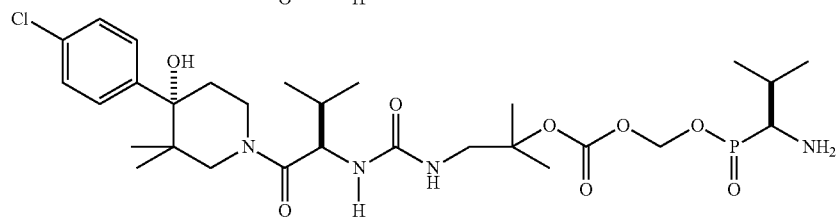

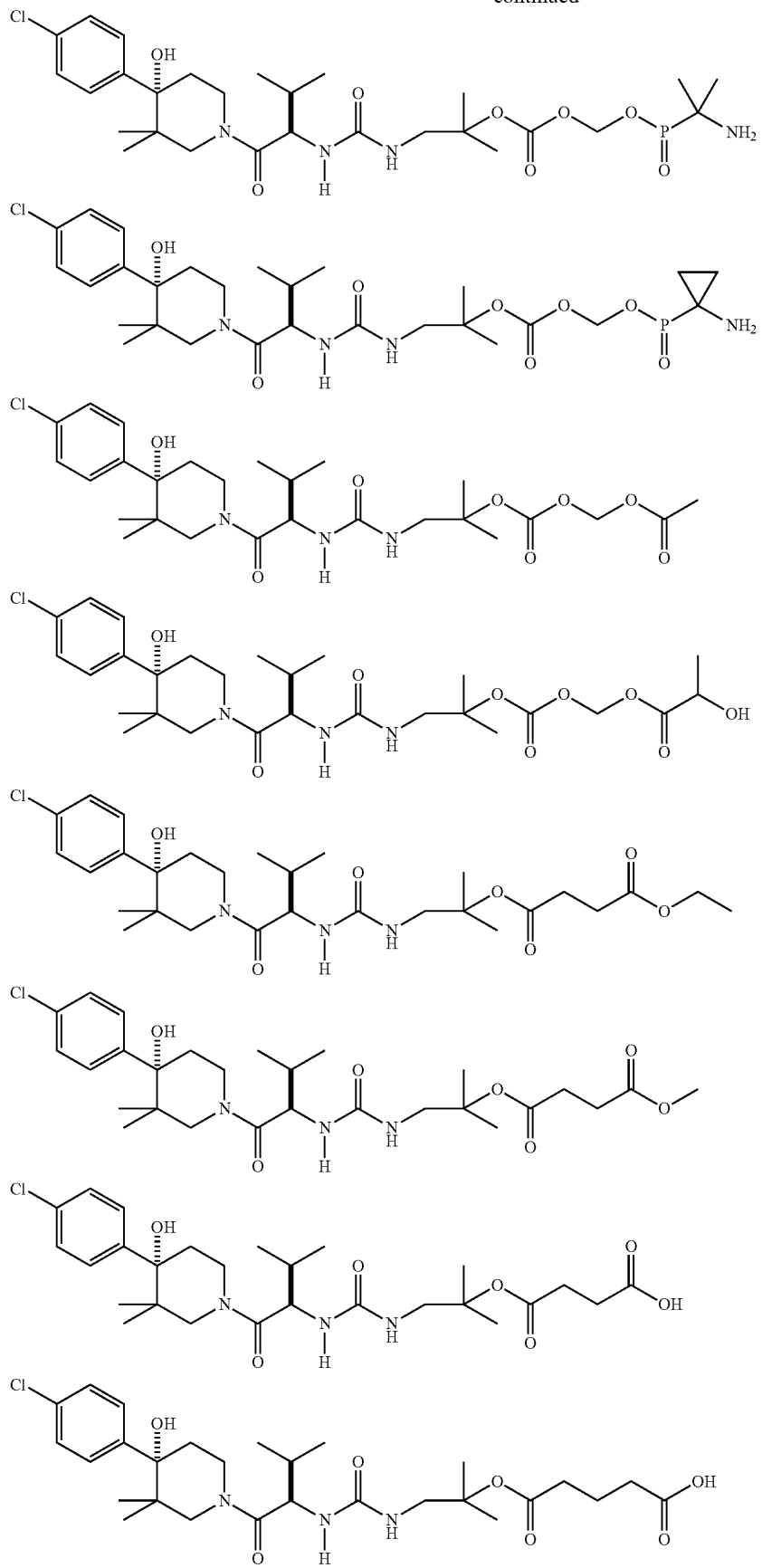

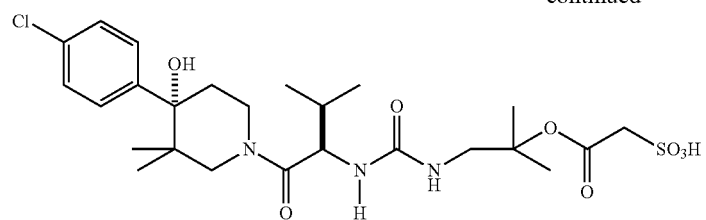
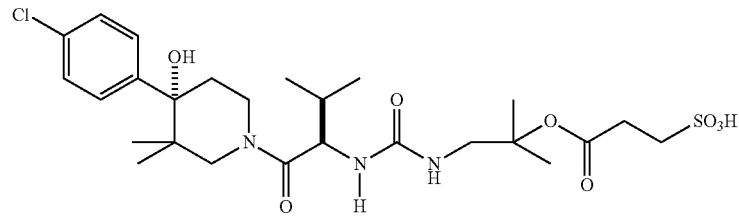
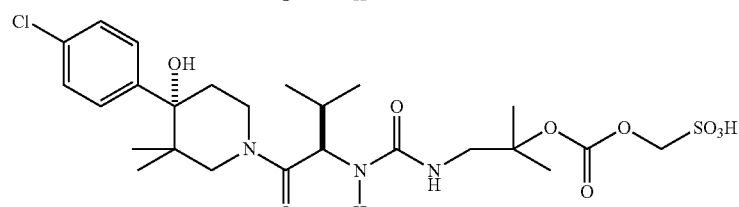
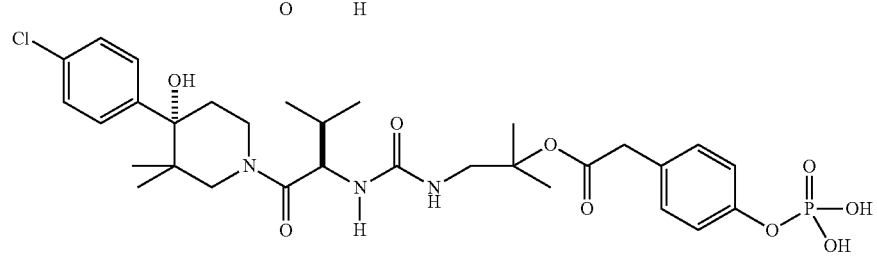
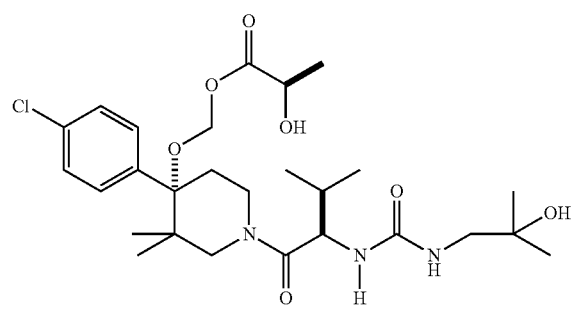
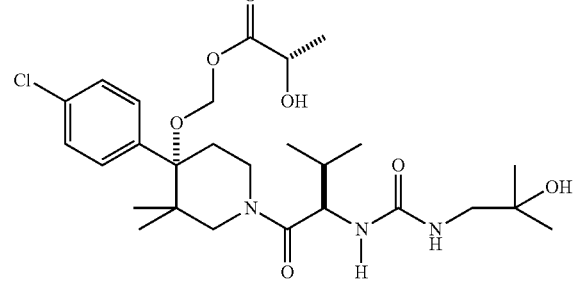
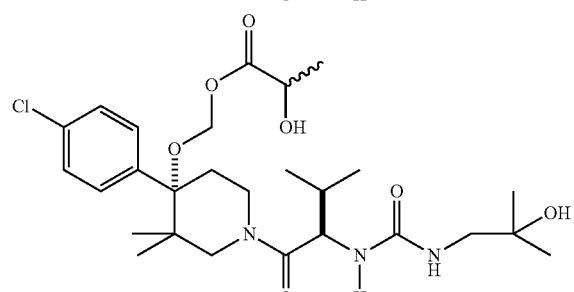
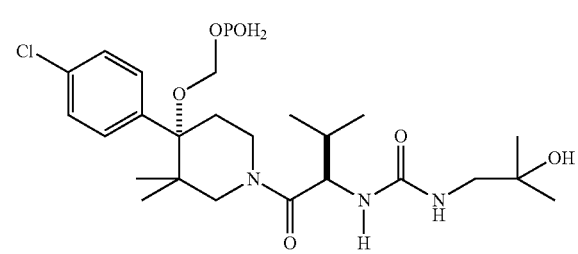
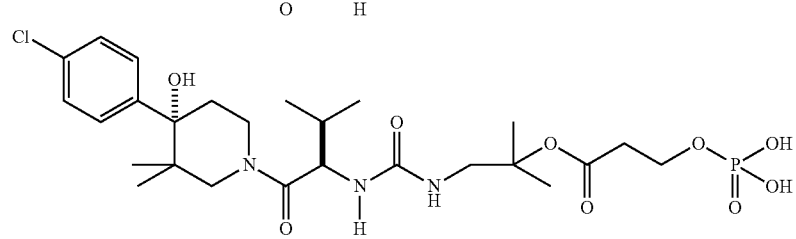

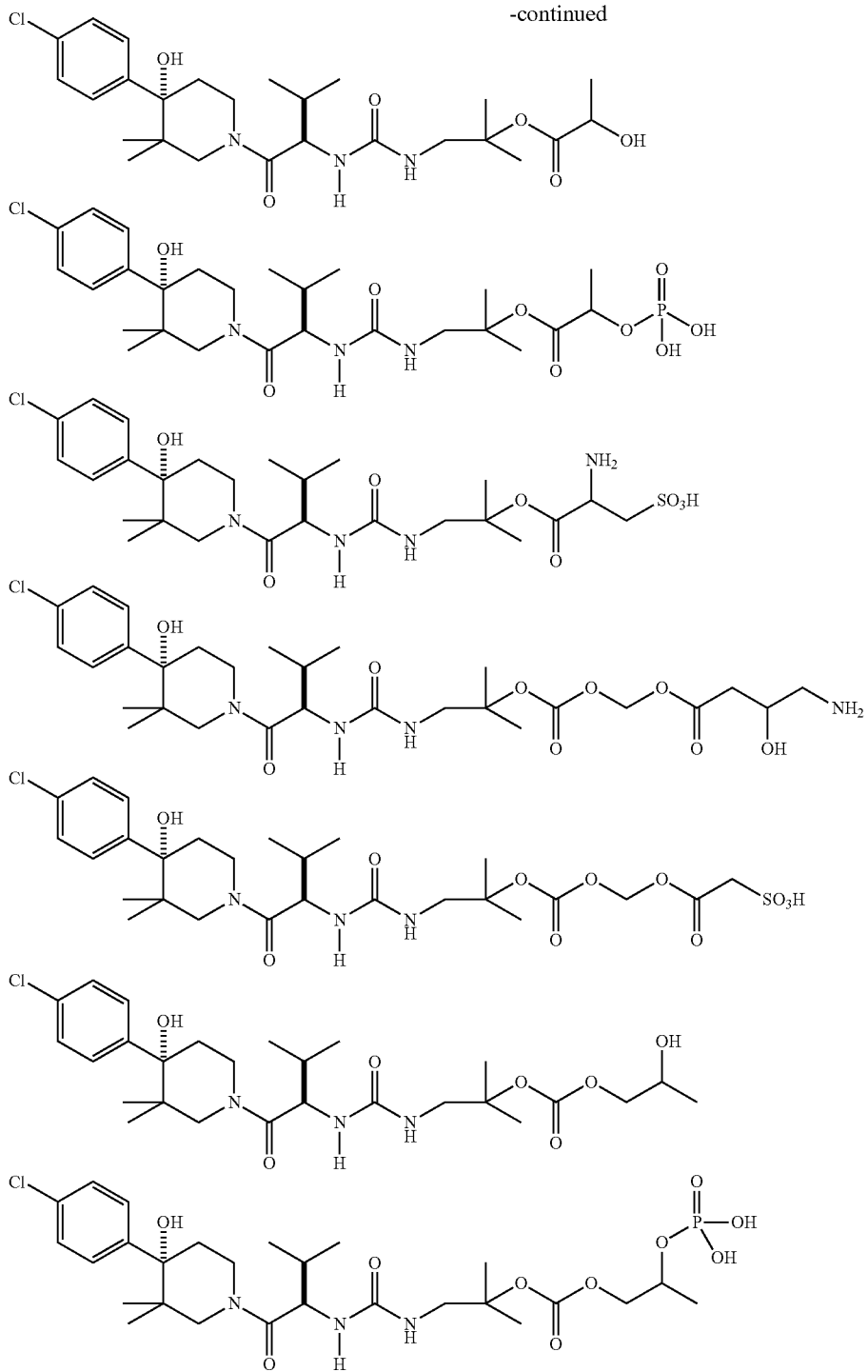
Preferred compounds of the invention include
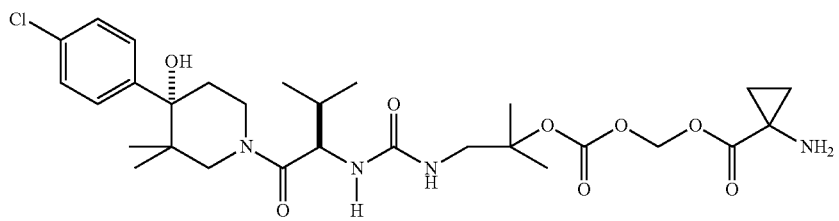

-continued
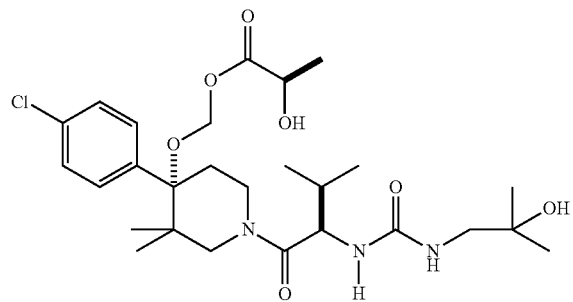
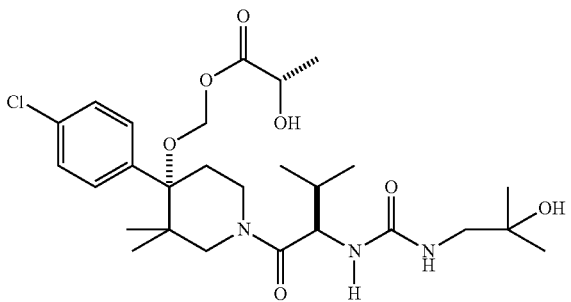
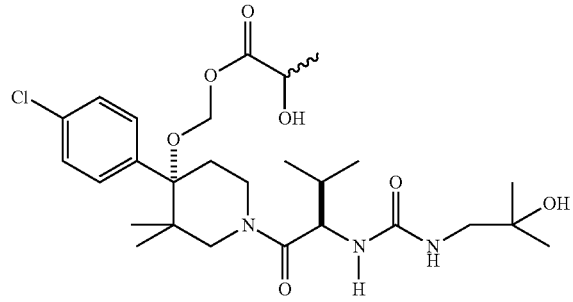
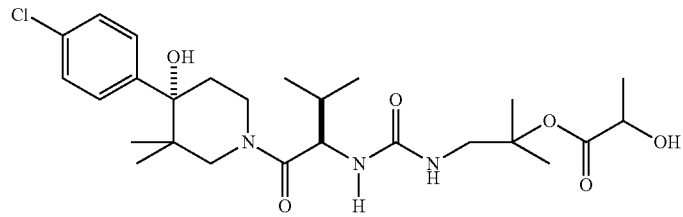
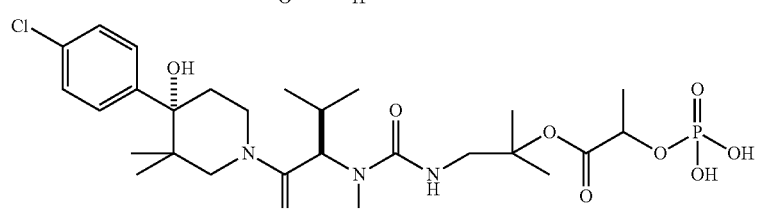
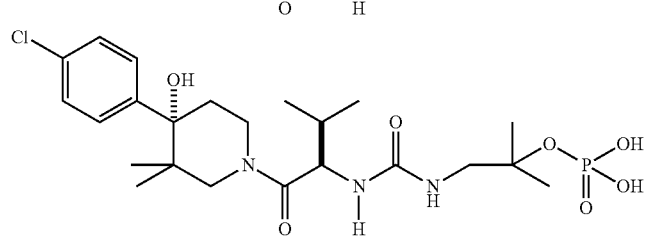
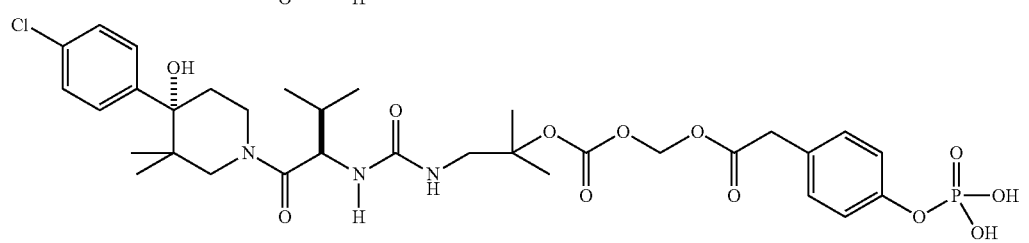
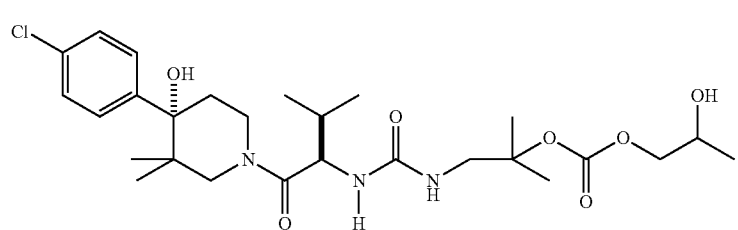

-continued

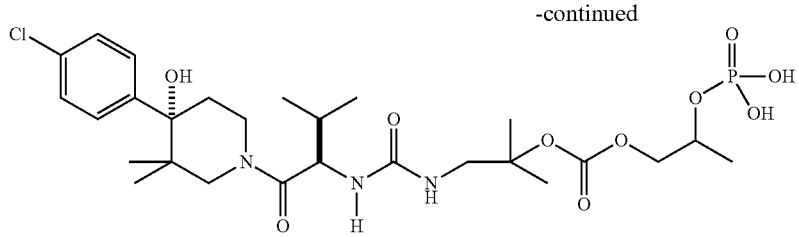

In another embodiment, the present invention is directed to a pharmaceutical composition, comprising a pharmaceutically acceptable carrier and a therapeutically effective amount of one or more prodrugs of a compound of formula (I).

In another embodiment, the present invention is directed to a method for modulation of chemokine or chemokine receptor activity comprising administering to a patient in need thereof a therapeutically effective amount of one or more prodrugs of the compound of formula (I).

In another embodiment, the present invention is directed to a method for modulation of CCR-1 receptor activity comprising administering to a patient in need thereof a therapeutically effective amount of one or more prodrugs of the compound of formula (I).

In another embodiment, the present invention is directed to a method for modulation of MIP-1α, MCP-3, MCP-4, RANTES activity, preferably modulation of MIP-1α activity, that is mediated by the CCR-1 receptor comprising administering to a patient in need thereof a therapeutically effective amount of one or more prodrugs of the compound of formula (I).

In another embodiment, the present invention is directed to a method for treating disorders, comprising administering to a patient in need thereof a therapeutically effective amount of one or more prodrugs of the compound of formula (I), wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, neuropathic pain, inflammatory bowel disease, alveolitis, ulcerative colitis, systemic lupus erythematosus, nephrotoxic serum nephritis, glomerulonephritis, asthma, multiple sclerosis, atherosclerosis, rheumatoid arthritis, restenosis, organ transplantation, psoriatic arthritis, multiple myeloma, allergies, for example, skin and mast cell degranulation in eye conjunctiva, hepatocellular carcinoma, colorectal cancer, osteoporosis, renal fibrosis, and other cancers, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a method for treating inflammatory diseases, comprising administering to a patient in need thereof a therapeutically effective amount of one or more prodrugs of the compound of formula (I).

In another embodiment, the present invention is directed to a method for treating inflammatory bowel disease, comprising administering to a patient in need thereof a therapeutically effective amount of one or more prodrugs of the compound of formula (I).

In another embodiment, the present invention is directed to a method for treating Crohn's disease, comprising administering to a patient in need thereof a therapeutically effective amount of one or more prodrugs of the compound of formula (I).

In another embodiment, the present invention is directed to a method for treating psoriasis, comprising administering to a patient in need thereof a therapeutically effective amount of one or more prodrugs of the compound of formula (I).

In another embodiment, the present invention is directed to a method for treating systemic lupus erythematosus, comprising administering to a patient in need thereof a therapeutically effective amount of one or more prodrugs of the compound of formula (I).

In another embodiment, the present invention is directed to a method for treating multiple sclerosis, comprising administering to a patient in need thereof a therapeutically effective amount of one or more prodrugs of the compound of formula (I).

In another embodiment, the present invention is directed to a method for treating rheumatoid arthritis, comprising administering to a patient in need thereof a therapeutically effective amount of one or more prodrugs of the compound of formula (I).

In another embodiment, the present invention is directed to a method for treating psoriatic arthritis, comprising administering to a patient in need thereof a therapeutically effective amount of one or more prodrugs of the compound of formula (I).

In another embodiment, the present invention is directed to a method for treating multiple myeloma, comprising administering to a patient in need thereof a therapeutically effective amount of one or more prodrugs of the compound of formula (I).

In another embodiment, the present invention is directed to a method for treating allergies, for example, skin and mast cell degranulation in eye conjunctiva, comprising administering to a patient in need thereof a therapeutically effective amount of one or more prodrugs of the compound of formula (I).

In another embodiment, the present invention is directed to a method for treating hepatocellular carcinoma, comprising administering to a patient in need thereof a therapeutically effective amount of one or more prodrugs of the compound of formula (I).

In another embodiment, the present invention is directed to a method for treating osteoporosis, comprising administering to a patient in need thereof a therapeutically effective amount of one or more prodrugs of the compound of formula (I).

In another embodiment, the present invention is directed to a method for treating renal fibrosis, comprising administering to a patient in need thereof a therapeutically effective amount of one or more prodrugs of the compound of formula (I).

In another embodiment, the present invention is directed to a method for treating inflammatory diseases, for example, inflammatory diseases which are at least partially mediated by CCR-1, comprising administering to a patient in need thereof a therapeutically effective amount of one or more prodrugs of the compound of formula (I).

In another embodiment, the present invention is directed to a method for modulation of CCR1 activity comprising administering to a patient in need thereof a therapeutically effective amount of one or more prodrugs of the compound of formula (I).

In another embodiment, the present invention is directed the use of one or more prodrugs of the compound of formula (I) in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, neuropathic pain, inflammatory bowel disease, alveolitis, ulcerative colitis, systemic lupus erythematosus, nephrotoxic serum nephritis, glomerulonephritis, asthma, multiple sclerosis, atherosclerosis, rheumatoid arthritis, restenosis, organ transplantation, psoriatic arthritis, multiple myeloma, allergies, for example, skin and mast cell degranulation in eye conjunctiva, hepatocellular carcinoma, colorectal cancer, osteoporosis, renal fibrosis and other cancers, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to one or more prodrugs of the compound of formula (I) for use in therapy.

In another embodiment, the present invention is directed to a pharmaceutical composition comprising one or more prodrugs of the compound of formula (I) and one or more active ingredients.

In another embodiment, the present invention is directed to a method for modulation of chemokine or chemokine receptor activity comprising administering to a patient in need thereof a therapeutically effective amount of a pharmaceutical composition comprised of one or more prodrugs of the compound of formula (I) and one or more active ingredients.

In another embodiment, the present invention is directed to a method for modulation of CCR-1 receptor activity comprising administering to a patient in need thereof a therapeutically effective amount of a pharmaceutical composition comprised of one or more prodrugs of the compound of formula (I) and one or more active ingredients.

In yet another embodiment, the present invention is directed to a method for modulation of MIP-1α, MCP-3, MCP-4, RANTES activity, preferably modulation of MIP-1α activity, that is mediated by the CCR-1 receptor comprising administering to a patient in need thereof a therapeutically effective amount of a pharmaceutical composition comprised of one or more prodrugs of the compound of formula (I) and one or more active ingredients.

In another embodiment, the present invention is directed to a method for treating a disorder, comprising administering to a patient in need thereof a therapeutically effective amount of a pharmaceutical composition comprised of one or more prodrugs of the compound of formula (I) and one or more active ingredients, wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, neuropathic pain, inflammatory bowel disease, alveolitis, ulcerative colitis, systemic lupus erythematosus, nephrotoxic serum nephritis, glomerulonephritis, asthma, multiple sclerosis, atherosclerosis, rheumatoid arthritis, restenosis, organ transplantation, psoriatic arthritis, multiple myeloma, allergies, for example, skin and mast cell degranulation in eye conjunctiva, hepatocellular carcinoma, colorectal cancer, osteoporosis, renal fibrosis and other cancers, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In yet another embodiment, the present invention, is directed to a method for treating inflammatory diseases, preferably, inflammatory diseases which are at least partially mediated by CCR-1, comprising administering to a patient in need thereof a therapeutically effective amount of a pharmaceutical composition comprised of one or more prodrugs of the compound of formula (I) and one or more active ingredients.

In another embodiment, the present invention is directed to a method for modulation of CCR-1 activity comprising administering to a patient in need thereof a therapeutically effective amount of a pharmaceutical composition comprised of one or more prodrugs of the compound of formula (I) and one or more active ingredients.

In another embodiment, the present invention is directed to the use of a pharmaceutical composition comprised of one or more prodrugs of the compound of formula (I) and one or more active ingredients in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, neuropathic pain, inflammatory bowel disease, alveolitis, ulcerative colitis, systemic lupus erythematosus, nephrotoxic serum nephritis, glomerulonephritis, asthma, multiple sclerosis, atherosclerosis, rheumatoid arthritis, restenosis, organ transplantation, psoriatic arthritis, multiple myeloma, allergies, for example, skin and mast cell degranulation in eye conjunctiva, hepatocellular carcinoma, colorectal cancer, osteoporosis, renal fibrosis and other cancers, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In still yet another embodiment, the present invention is directed to the use of a pharmaceutical composition comprised of one or more prodrugs of the compound of formula (I) and one or more active ingredients in therapy.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent as known to one of ordinary skill in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference. Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MIP-1α or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of the invention were prepared as shown in the following Examples, reaction schemes and descriptions thereof, as well as relevant literature procedures that may be used by one skilled in the art. Exemplary reagents and procedures for these reactions appear hereinafter.

Compounds of the formula 1.3 can be prepared according to the method outlined in Scheme 1. Starting with Compound 1, reaction with an appropriate phosphorylating agent followed by oxidation with, for example, hydrogen peroxide, can furnish the protected phosphate compound 1.2. Protecting groups that can be used for this transformation are allyl and benzyl, for example and it is understood that one skilled in the art of organic synthesis would be able to utilize other protecting groups for this process. Removal of the protecting groups can furnish the compound of the formula 1.3.

Scheme 1

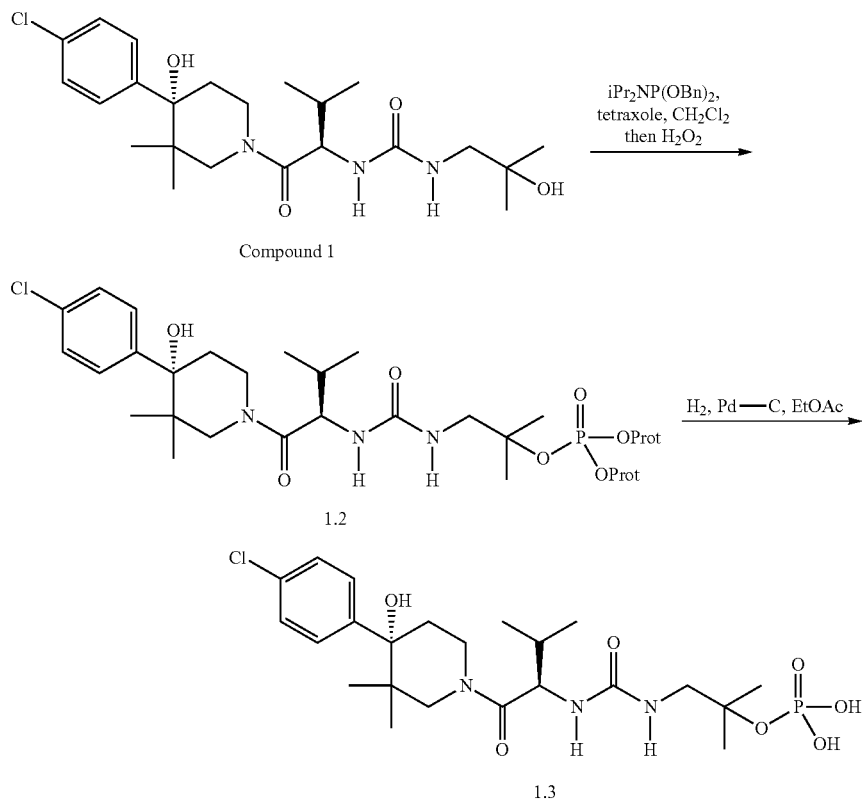

Compounds of the formulas 2.1, 2.3 and 2.4 can be prepared according to the methods outlined in Scheme 2. Coupling of compound 1 with a variety of carboxylic acids, anhydrides or acid chlorides can furnish compounds of the general formula 2.1 which may need further modification via hydrolysis to the final analogs. Standard coupling of protected amino acid derivatives followed by deprotection of the amino group using standard methods can furnish compounds of the formula 2.3. Reaction of compound 1 with a functionalized chloroformate such as 2.4 can provide compound 2.2 which can be further reacted with a nucleophile, such as morpholine, to provide compound 2.5.

Scheme 2

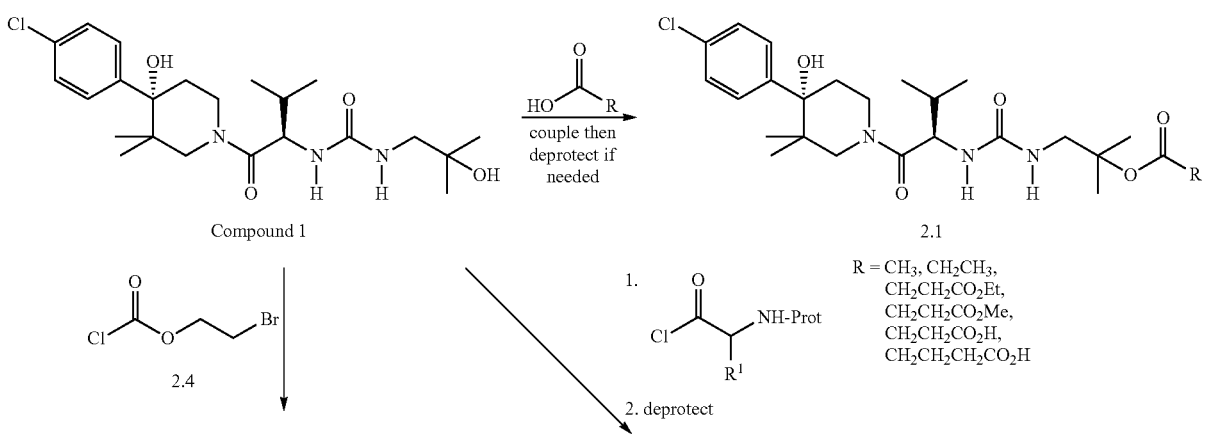

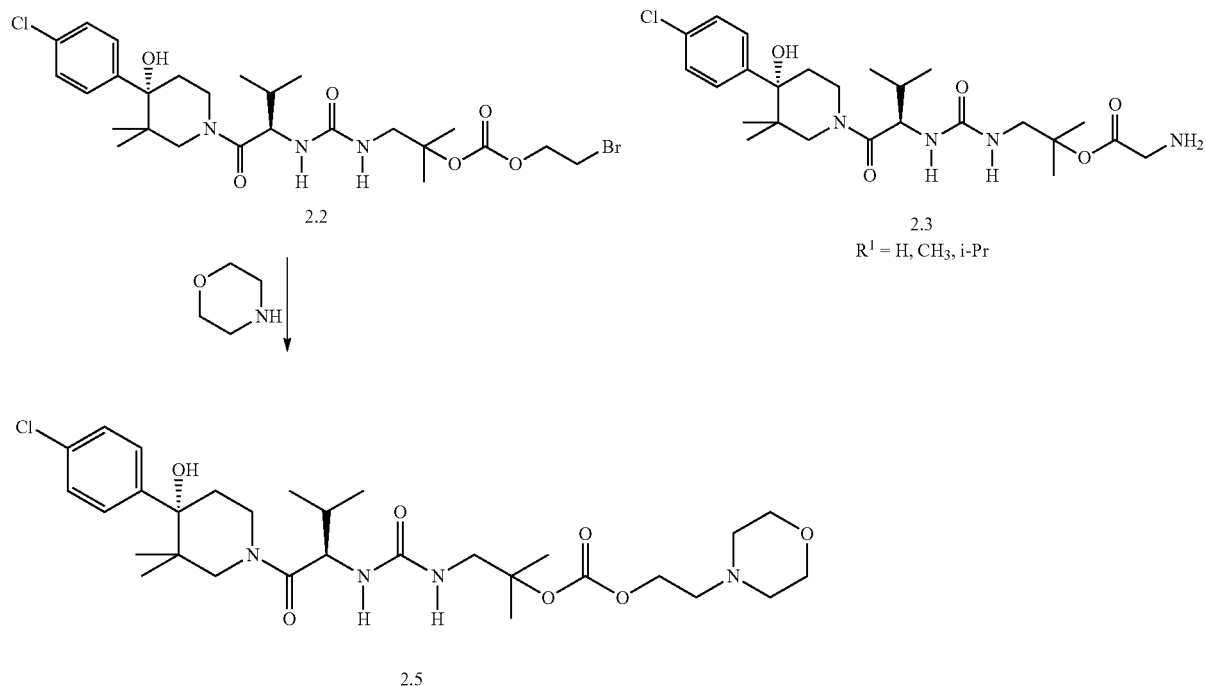

Compounds of the general structures 3.4 and 3.5 can be prepared according to the methods outlined in Scheme 3. The methylthiomethyl ether 3.1 can be prepared by reacting compound 3.1 with DMSO and acetic anhydride. Reaction of compound 3.3 with an appropriate activating reagent, such as NBS or CuBr$_2$, followed by reaction with a nucleophile such as a salt of phosphoric acid or lactic acid or an amino acid can provide the compounds 3.4 and 3.5.

Scheme 3

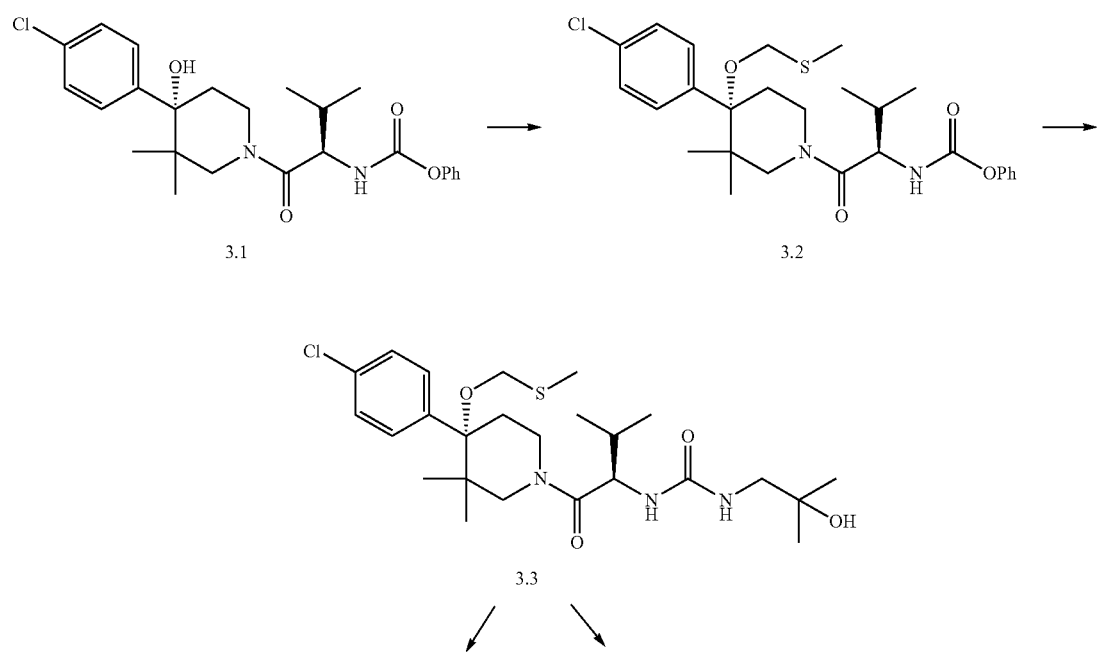

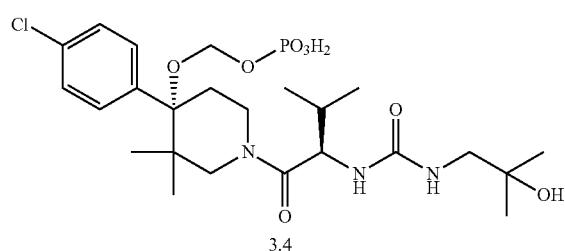

3.4

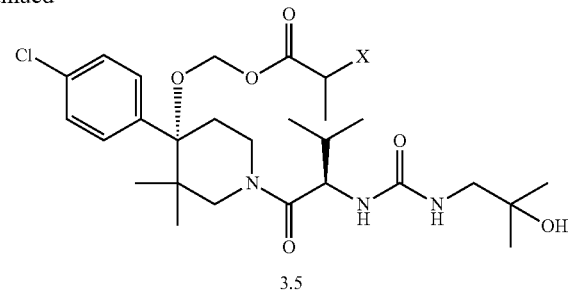

3.5

X = OH, NH₂

Compounds of the formula 4.3 can be prepared according to the methods outlined in Scheme 4. Reaction of compound 1 with chloromethyl chloroformate in an appropriate solvent in the presence of a base, such as pyridine, can provide compound 4.1. Reaction of 4.1 with a protected amino acid derivative in the presence of a base, such as $K_2CO_3$, can provide 4.2. Deprotection of the amino acid component can provide compound 4.3. Compounds that can be prepared according to this method are also shown in Scheme 4.

Scheme 4

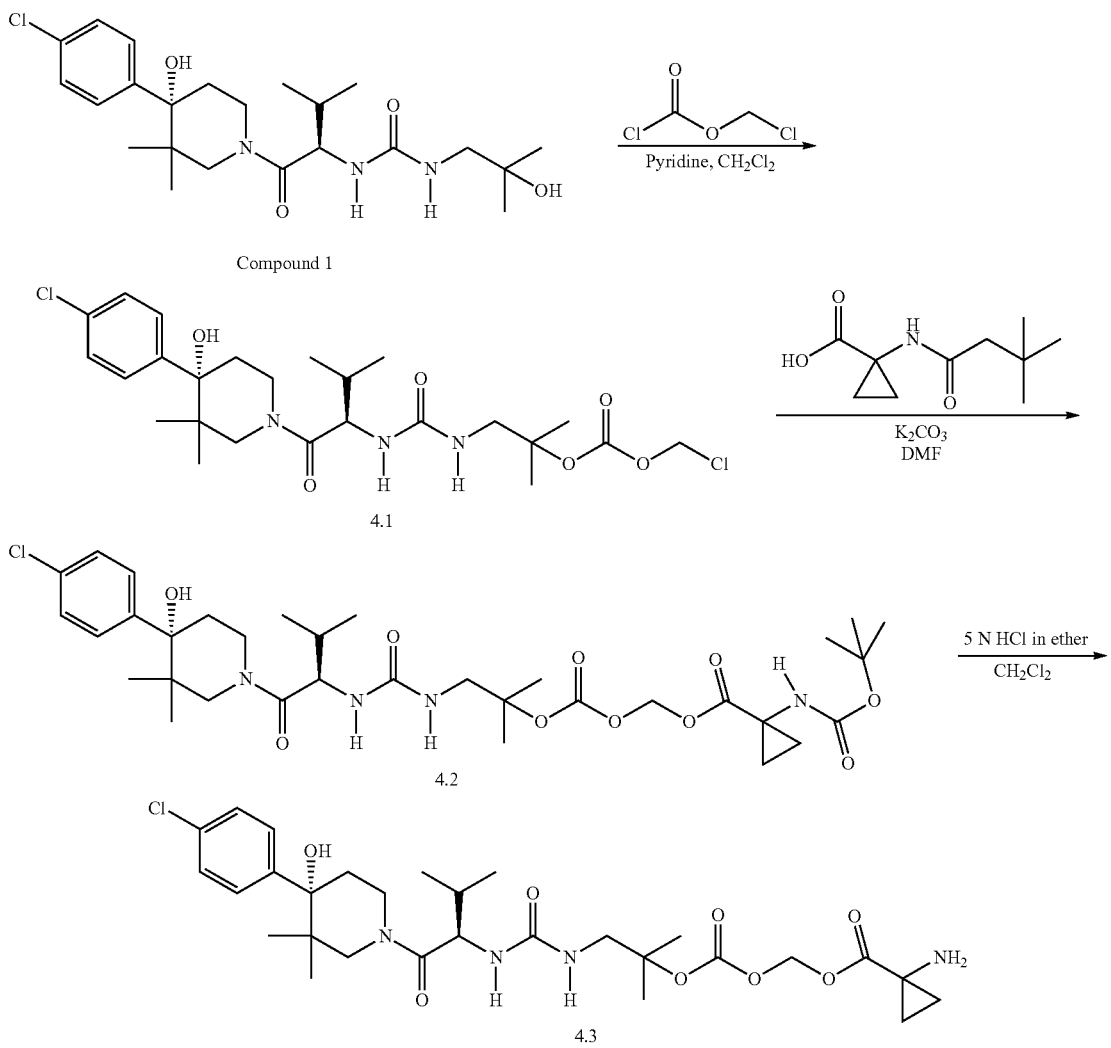

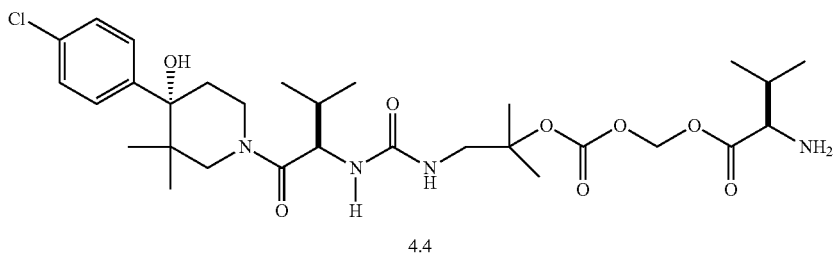

4.4

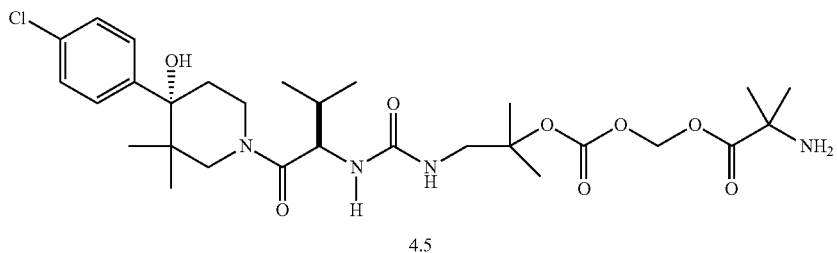

4.5

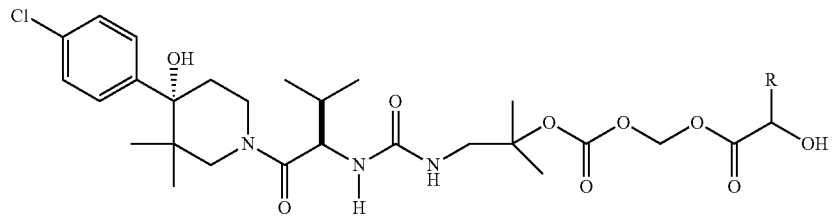

4.6, R = H
4.7, R = CH₃

Compound 4.1 can be used as an intermediate to prepare a variety of additional prodrug analogs as shown in Scheme 5. For example, reaction of 4.1 with fumaric acid in the presence of a base, such as TEA, can provide compound 5.1. Additionally, direct reaction with phosphoric acid and TEA can provide 5.2. Compounds of the formula 5.3 can be prepared by reacting 4.1 with an appropriately protected and functionalized carboxylic acid in the presence of a base which in turn can be deprotected to reveal the compound 5.3. Additionally, compounds of the formula 5.4 can be prepared by reacting an appropriately functionalized phenylacetic acid with compound 4.1 then unmasking the phosphate via hydrogenation to reveal compound 5.4.

Scheme 5
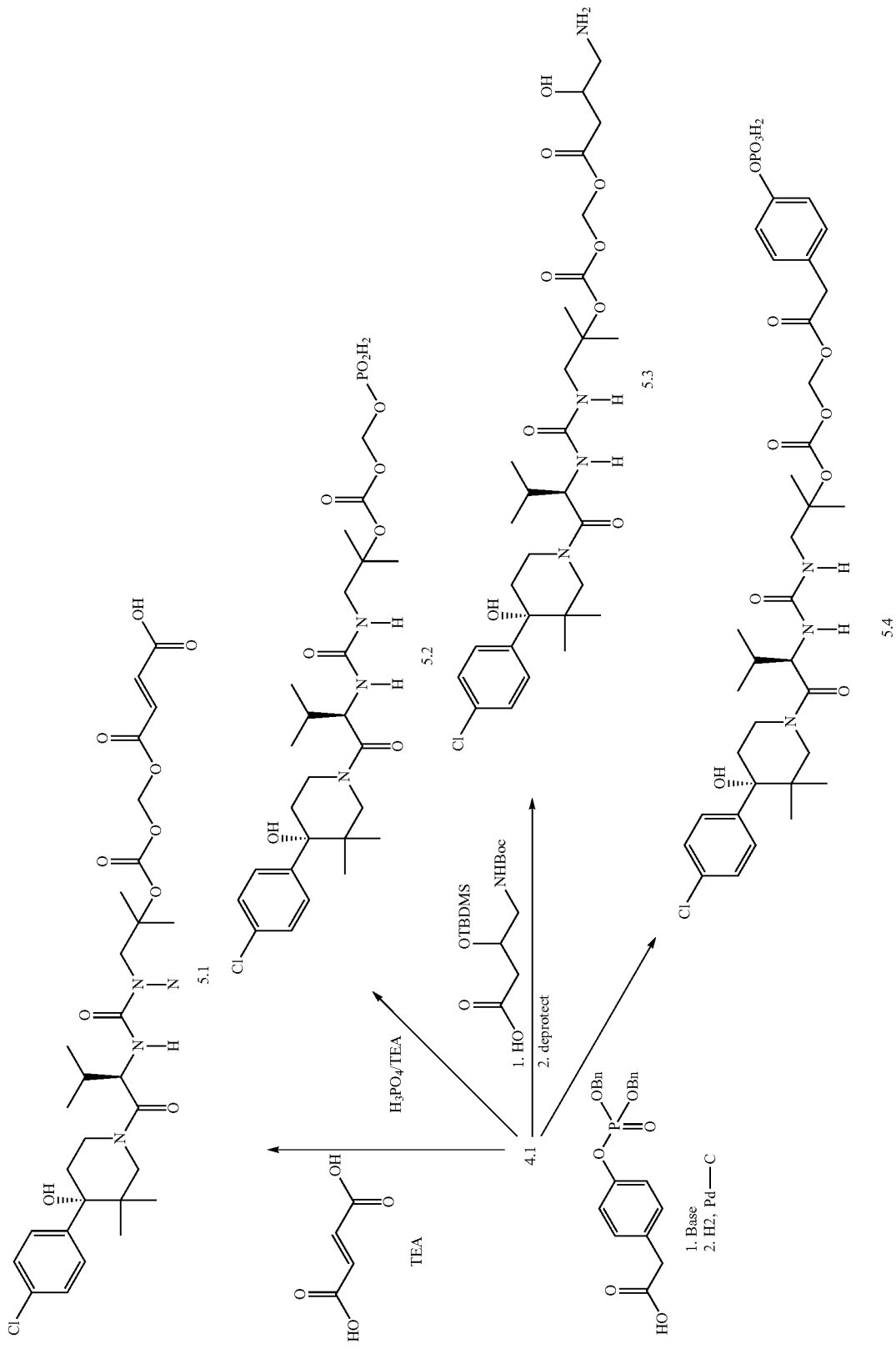

Compound 4.1 can also be utilized to prepare additional compounds such as the analogs shown in Scheme 6. Direct displacement of the chloride with an acid followed by oxidation of the sulfur moiety and deprotection can furnish the compounds 6.1 and 6.2. Conversion of the chloride 4.1 to the more reactive iodide with NaI followed by reaction with Na₂SO₃ can provide the compound 6.3.

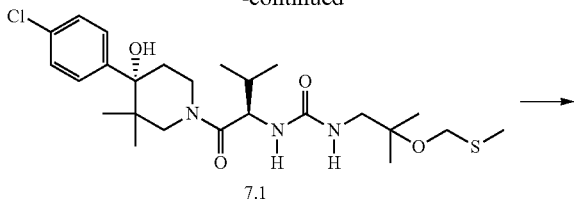

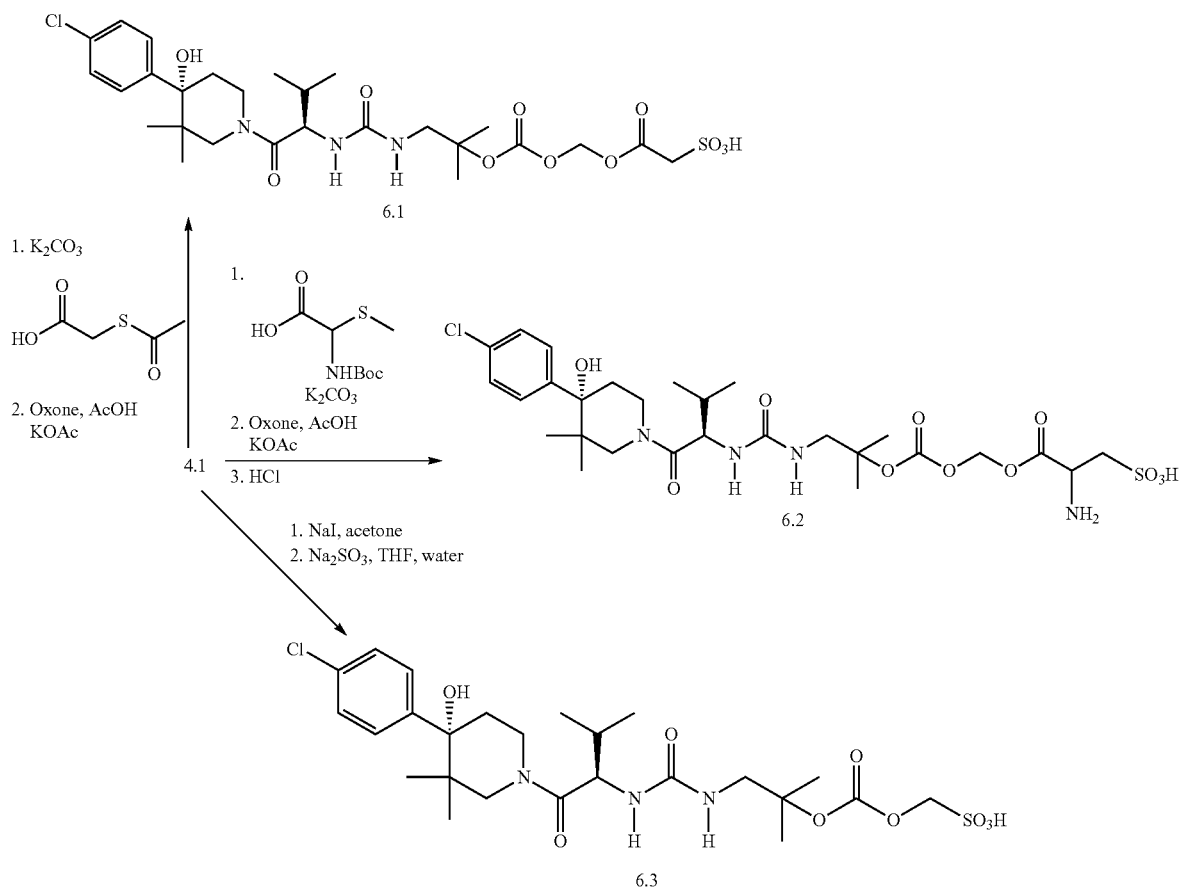

Scheme 6

Additionally, compounds of the formula 7.2 can be prepared by reaction of compound 1 with acetic anhydride and DMSO to give the methylthiomethyl ether 7.1 which in turn can be reacted with an activating agent, such as NBS or NIS, followed by reaction with phosphoric acid and a base to furnish 7.2.

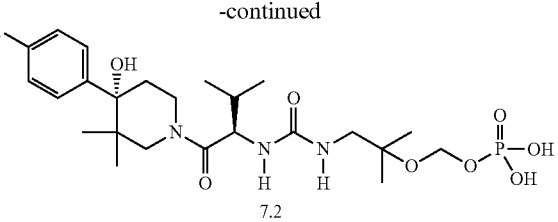

Scheme 7

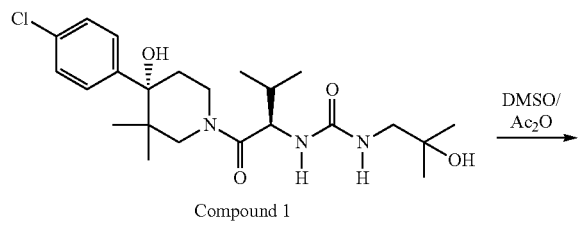

Additional prodrugs of compound 1 can be prepared according to the methods outline in Scheme 8. Reaction of compound 1 with a protected lactic acid derivative, such as benzyl lactic acid, with a coupling agent can form the ester 8.1. Removal of the protecting group followed by phosphate formation on the secondary alcohol can furnish the alcohol 8.2 and phosphate 8.3 respectively. Similarly, compound 1 can be reacted with a protected hydroxyl acid, such as 3-O-benzyl propionic acid to furnish the ester 8.4. Following deprotection to the alcohol 8.5 and conversion to the phosphate using standard conditions compound 8.6 can be obtained.

of a base, such as pyridine, can provide 9.2. Reaction with Na₂SO₃ in an appropriate solvent can afford the sulfonic acid derivative 9.2. Prodrugs of the formula 9.5 can be prepared by

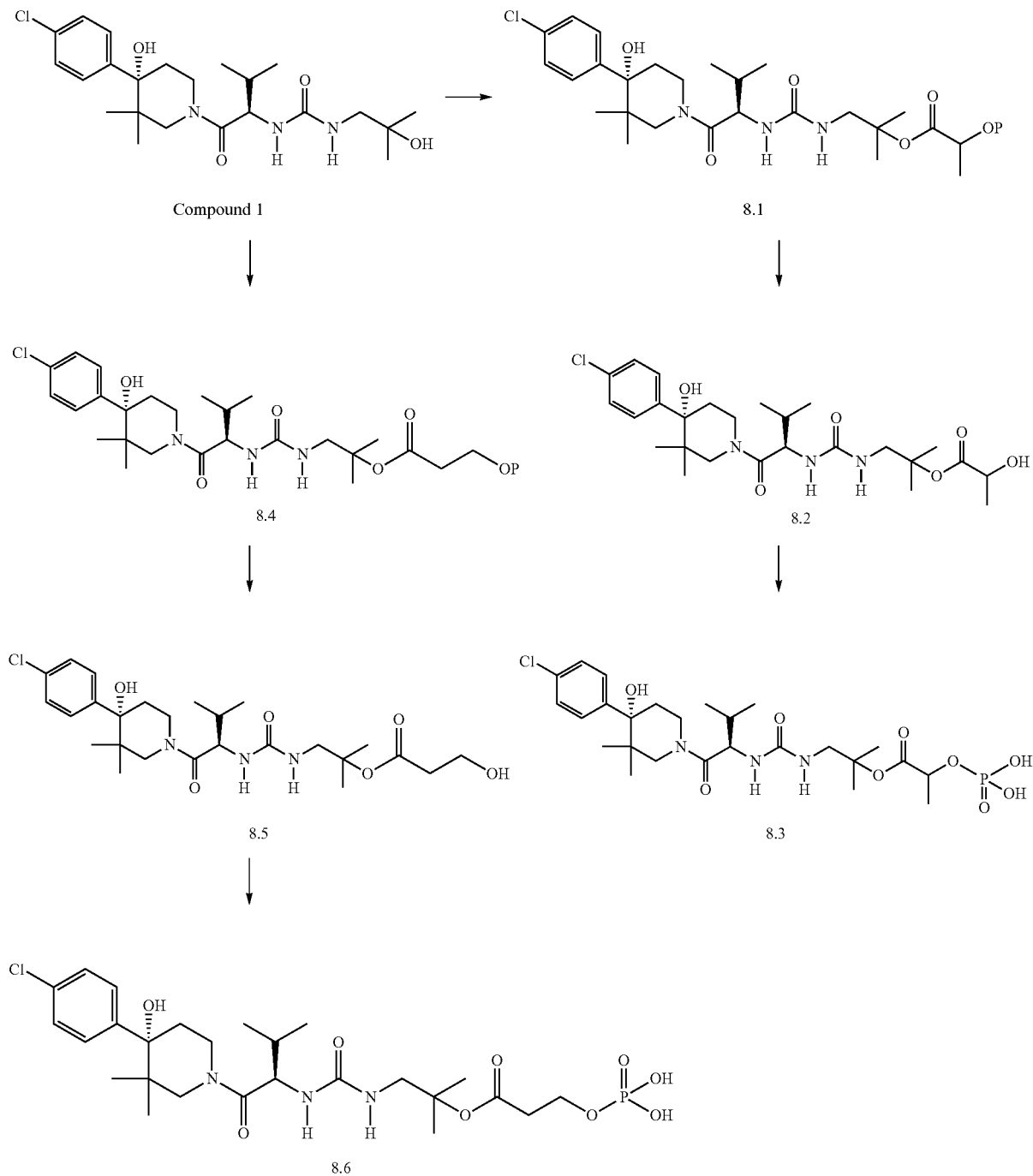

Scheme 8

P = protecting group

Sulfonic acid derived prodrugs of compound 1 can be prepared according to the methods outline in Scheme 9. Reaction of compound 1 with chloroacetyl chloride in the presence first reacting compound 1 with acryloyl chloride to furnish 9.3. Reaction of 9.3 with a sulfur nucleophile, such as thioacetic acid, can provide compound 9.4 which can be converted to the sulfonic acid using standard methods (KOAc, AcOH, Oxone).
Additional prodrug analogs can be prepared according to the methods outlined in Scheme 10. Reaction of compound 1
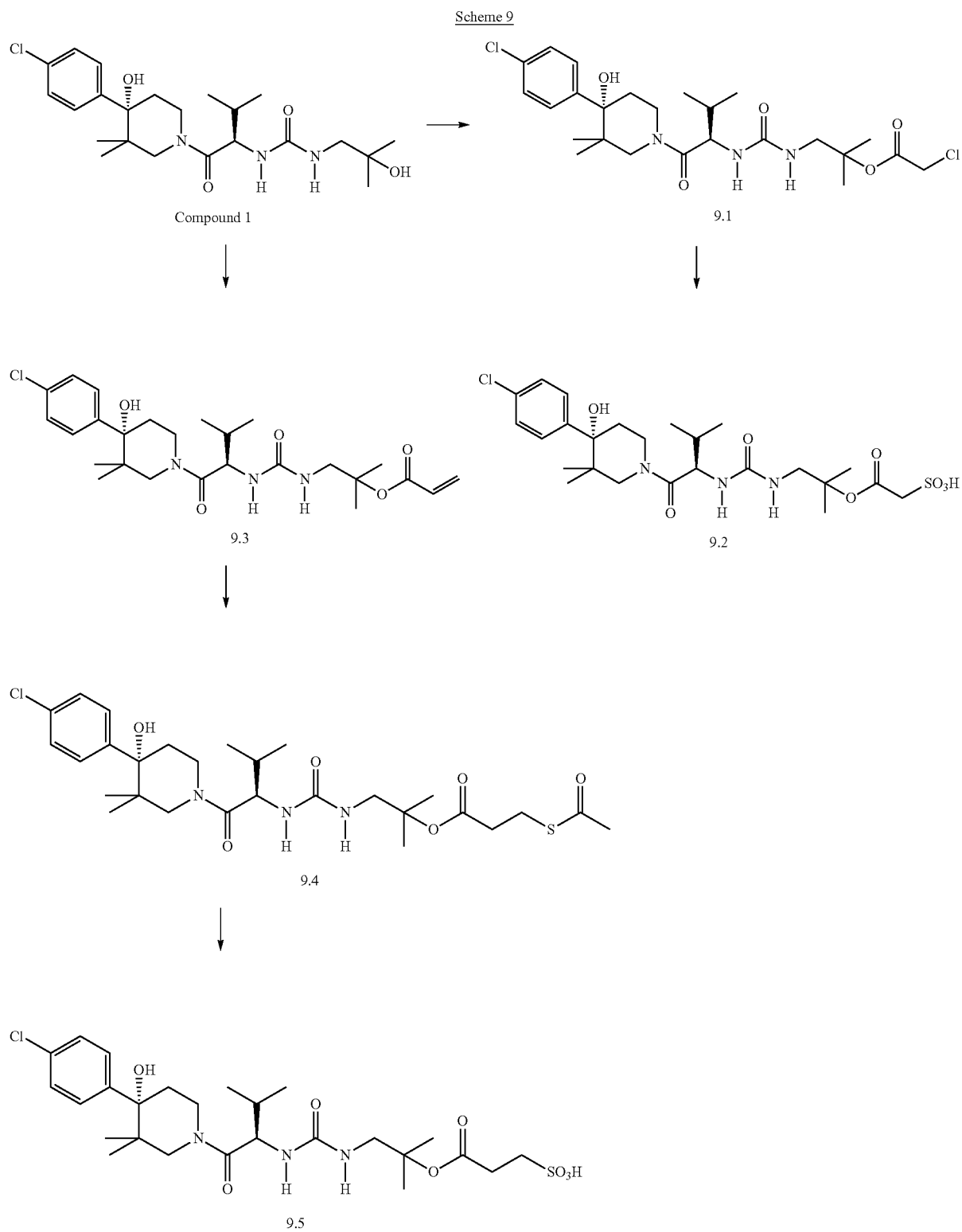

with an appropriately protected 4-hydroxyphenylacetic acid derivative can provide compound 10.1. Removal of the protecting group can furnish the phenol compound 10.2 which can be converted to the phosphate using similar methods to the ones described previously.

Additional carbonate derived prodrugs of compound 1 can be prepared according to the methods outlined in Scheme 11. Reaction of compound 1 with allyl chloroformate in the presence of a base can provide compound 11.1 which can then be converted to the ketone 11.2 using known methods (PdCl2,

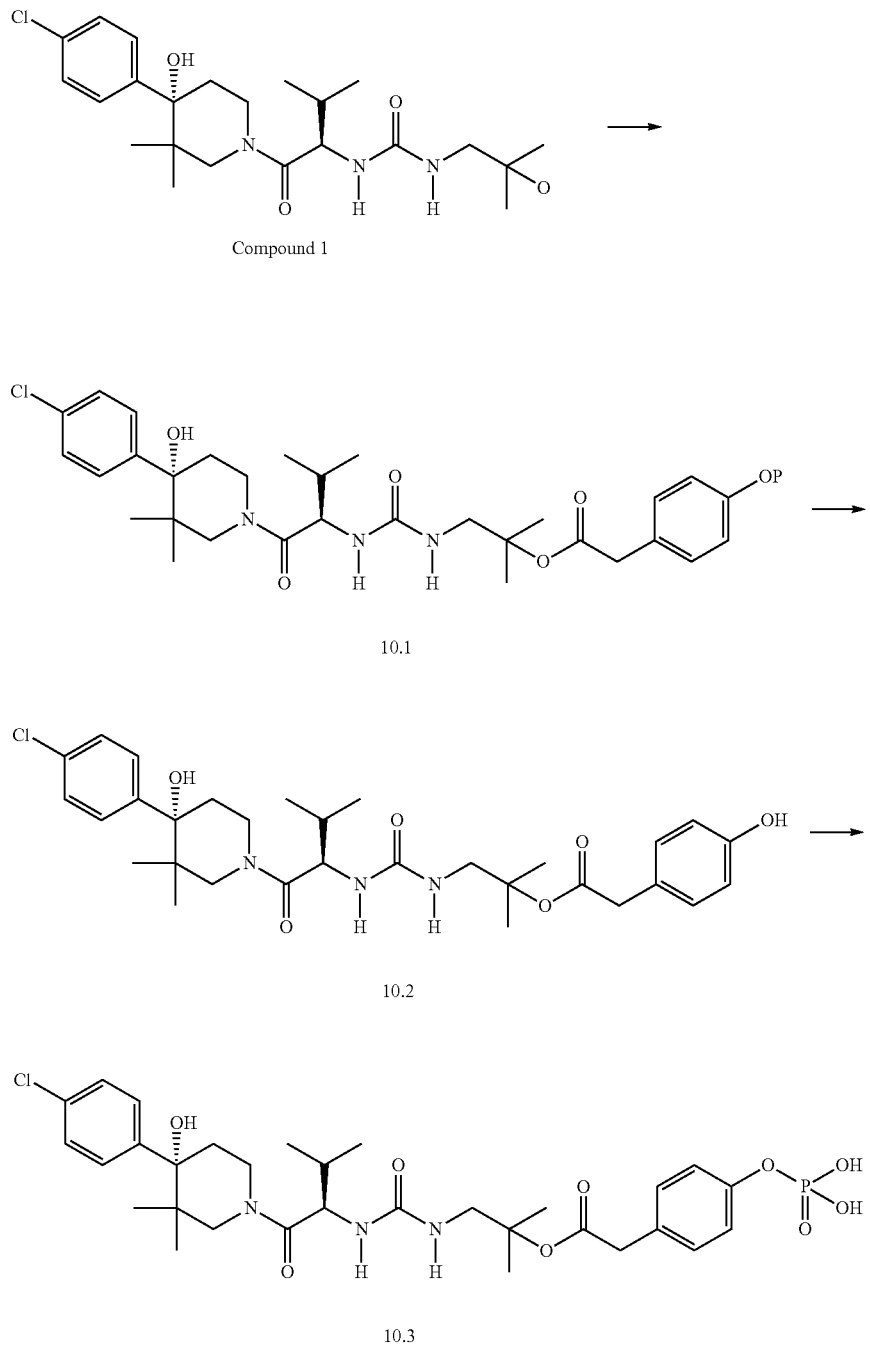

P = protecting group

CuCL2, THF, water, for example). The ketone can then be reduced to the alcohol 11.3 which in two additional steps (phosphorylation and deprotection) can provide the phosphate prodrug 11.4
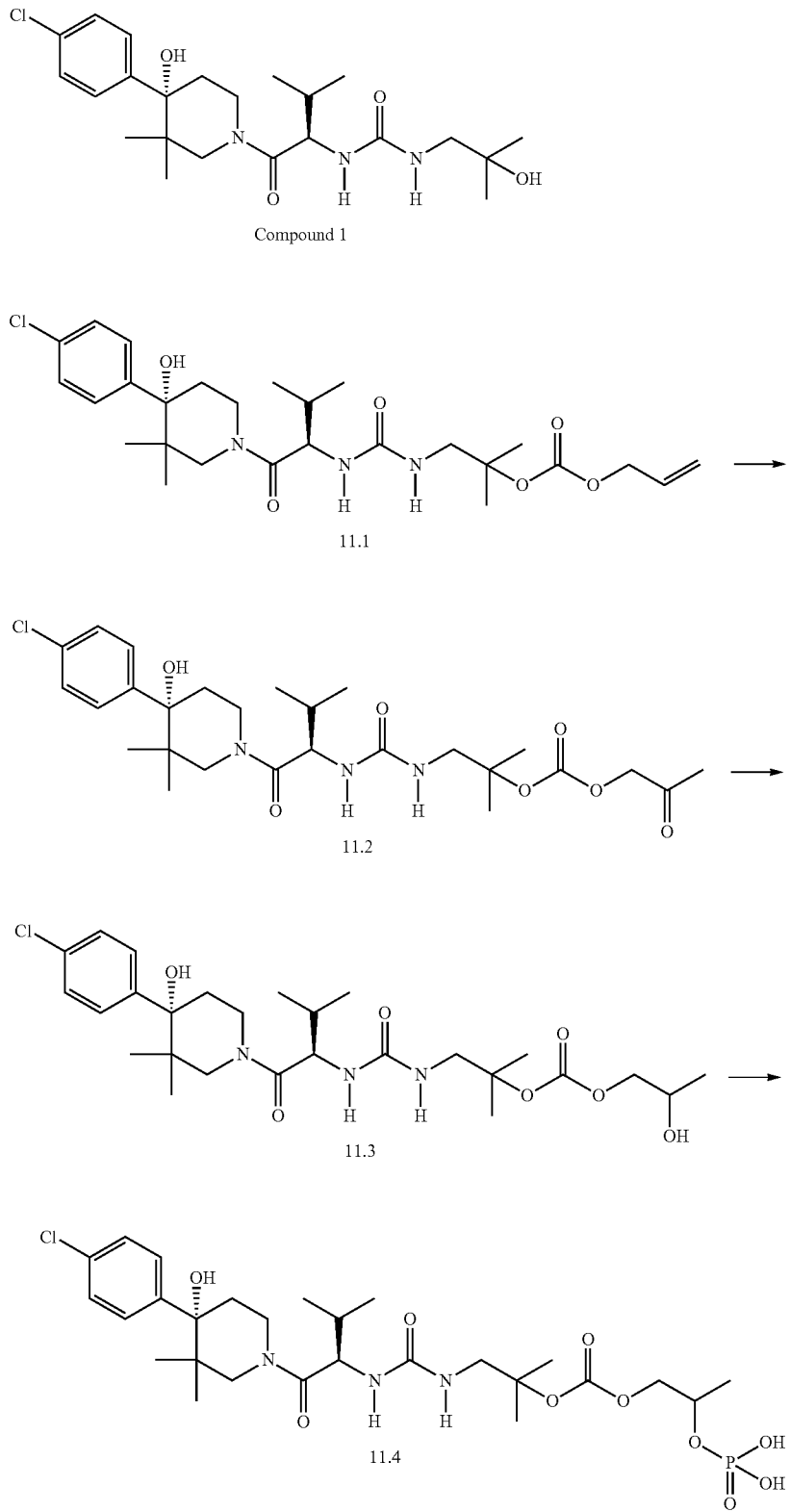

EXAMPLE 1

Step 1: tert-Butyl 3,3-dimethyl-4-oxopiperidine-1-carboxylate

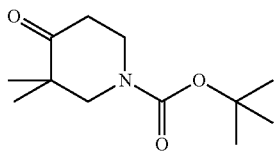 [SMILES: CC(C)(C)OC(=O)N1CCC(=O)C(C)(C)C1]

A solution of tert-butyl 4-oxopiperidine-1-carboxylate (52.47 g, 263 mmol) in THF (1000 mL) was cooled to 0° C. and treated with sodium hydride (60% suspension in mineral oil) (22.12 g, 553 mmol) in 4 equal portions at 5 minute intervals. The resulting suspension was stirred at 0° C. for 45 minutes ("min."), and then treated with the dropwise addition of iodomethane (41.2 ml, 658 mmol). The mixture was stirred for 1 hour ("h" or "hr"), and then allowed to come to room temperature ("rt"). Ninety minutes after the ice bath was removed, a rapid exotherm (20-40° C. in 3 minutes) and vigorous gas evolution was observed. The ice bath was replaced, and the mixture was allowed to stir overnight as it slowly warmed to room temperature. The reaction was quenched with saturated ammonium chloride (200 mL) then treated with enough water to dissolve the salts which had precipitated. The layers were separated and the organic phase was concentrated in vacuo. The aqueous phase was extracted with ethyl acetate, and this extract was combined with the residue from the first organic phase. The resulting solution was diluted with 500 ml ethyl acetate, and the mixture was washed 2 times ("x") with water, once with brine, dried over sodium sulfate and then concentrated in vacuo to yield a viscous oil which solidified upon standing. The solidified cake was dissolved in 100 mL of boiling hexanes, and the resulting solution was allowed to cool to room temperature where it stood overnight. After this time, crystals that had precipitated were collected by filtration, rinsed with a small amount of ice-cold hexanes, and dried to yield the title compound as a powder (19.5 g, 86 mmol, 32.6% yield). MS (ES+)=172, 154.

Step 2: (±)-tert-Butyl 4-(4-chlorophenyl)-4-hydroxy-3,3-dimethylpiperidine-1-carboxylate

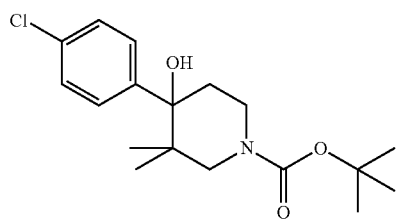 [SMILES: CC(C)(C)OC(=O)N1CCC(O)(c2ccc(Cl)cc2)C(C)(C)C1]

A solution of 4-bromochlorobenzene (136.6 g, 0.71 mol) in anhydrous THF (1000 mL) was cooled to −78° C., and then treated dropwise with a 1.6 M solution of n-butyllithium in hexanes (466 mL, 0.75 mol) at a rate which maintained the internal temperature below −60° C. The resulting mixture was stirred at −78° C. for 1.5 hours, during which a precipitate was observed. The resulting suspension was treated dropwise with a solution of tert-butyl 3,3-dimethyl-4-oxopiperidine-1-carboxylate (73.7 g, 0.32 mol) in anhydrous THF (400 mL) at a rate which maintained the internal temperature below −60° C. The mixture was stirred at −78° C. for 2 hours, during which a clear solution was observed. The reaction mixture was quenched with saturated ammonium chloride (300 mL) and the resulting mixture was allowed to come to room temperature. The aqueous and organic layers were separated, and the organic phase was concentrated in vacuo to yield a residue. The aqueous phase was extracted 2× with ethyl acetate (300 mL). The combined extracts were added to the residue from the original organic phase, and the resulting mixture was diluted to 1200 mL with ethyl acetate. The resulting solution was washed 2× with water (300 mL), once with brine, dried over sodium sulfate, and concentrated in vacuo to yield a residue. The residue was digested with boiling hexanes (300 mL), and the resulting suspension was cooled to room temperature. Once at the prescribed temperature, white solids were collected by filtration, and washed 2× with hexanes and then air dried to yield the title compound as a powder (93.7 g, 85% yield).

Step 3: (±)-4-(4-Chlorophenyl)-3,3-dimethylpiperidin-4-ol

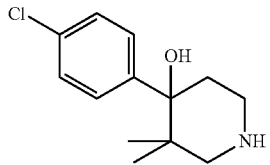

A solution of (±)-tert-butyl 4-(4-chlorophenyl)-4-hydroxy-3,3-dimethylpiperidine-1-carboxylate (93.7 g, 0.276 mol) in dioxane (100 mL) was treated with 4 M HCl solution in dioxane (275 mL, 1.1 mol). The resulting mixture was stirred at room temperature for four hours. After this time, the mixture was concentrated in vacuo, and then concentrated 3× from methylene chloride (200 mL) to remove residual HCl. The resulting residue was stirred in 1 M NaOH (500 mL), and the resulting suspension was extracted 4× with 500 mL of ethyl acetate. The combined organic phases were washed with brine, dried over sodium sulfate, and concentrated in vacuo to yield the title compound (66.8 g, quantitative yield) as a solid.

Step 4: (S)-4-(4-Chlorophenyl)-3,3-dimethylpiperidin-4-ol

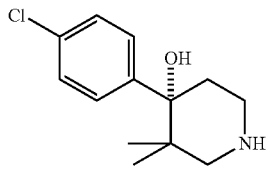 [SMILES: CC1(C)CNCC[C@]1(O)c1ccc(Cl)cc1]

A suspension of (±)-4-(4-chlorophenyl)-3,3-dimethylpiperidin-4-ol (175 g) and L-tartaric acid (0.9 equiv) in MEK (3.22 L) was heated to reflux. Once at the prescribed temperature, water (100 mL) was added to achieve a solution. The resulting solution was heated at reflux for 1 h and then allowed to cool to room temperature where it stirred for 48 h.

After this time, the resulting slurry was filtered and the collected solids were dried under vacuum to give 123.4 grams of the tartaric acid salt. This material was combined with another run of the same scale and the combined solids were suspended in MEK (2.55 L) and water (0.25 L). The resulting solution was heated to reflux and additional water (0.2 L) was added to solubilize the mixture. The solution was heated at reflux for 2 h and then allowed to cool to room temperature, where it stirred over the weekend. At the conclusion of this period, the resulting solids were collected by filtration and dried to give 219 g of the salt. The salt was divided into two equal portions. Each portion was suspended in water (2 L) and then 50% NaOH was added to precipitate the free base of the piperidine. After filtering and drying, 126.3 g of the title compound was isolated (~72% yield, >99% ee).

Step 5: tert-Butyl (R)-1-((S)-4-(4-chlorophenyl)-4-hydroxy-3,3-dimethylpiperidin-1-yl)-3-methyl-1-oxobutan-2-ylcarbamate

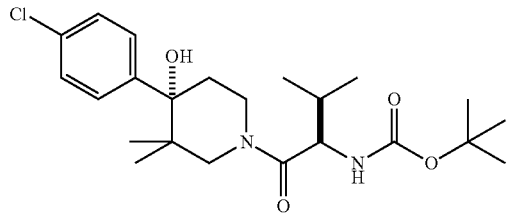 [SMILES: CC(C)[C@@H](NC(=O)OC(C)(C)C)C(=O)N1CC[C@](O)(c2ccc(Cl)cc2)C(C)(C)C1]

To a 3 L three neck roundbottom ("RB") flask was added (R)-2-(tert-butoxycarbonylamino)-3-methylbutanoic (39.8 g, 183 mmol), CH$_2$Cl$_2$ (1.6 L), (S)-4-(4-chlorophenyl)-3,3-dimethylpiperidin-4-ol (40.0 g, 167 mmol), EDC (70.4 g, 367 mmol), and HOBt (56.2 g, 416 mmol). Upon completion of addition, the reaction mixture was stirred for 30 min. at rt. After this time, triethyl amine (TEA, 93 mL, 668 mmol) was added. The resulting mixture was stirred at room temperature for 20 h. At the conclusion of this period, the reaction mixture was washed with Na$_2$CO$_3$ (3×300 mL, note: the first Na$_2$CO$_3$ wash, was vacuum filtered and the resulting filtrate was back extracted with CH$_2$Cl$_2$), 1N HCl (3×300 mL), water (400 mL) and brine (300 mL). The resulting solution was dried over Na$_2$SO$_4$ and concentrated to a semi-solid (106 g, theoretical yield was 73.2 g). The semi-solid was reacted in the next step without further purification.

Step 6: (R)-2-Amino-1-((S)-4-(4-chlorophenyl)-4-hydroxy-3,3-dimethylpiperidin-1-yl)-3-methylbutan-1-one, HCl

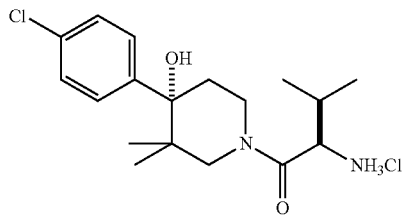

To a 1000 mL RB flask was added tert-butyl (R)-1-((S)-4-(4-chlorophenyl)-4-hydroxy-3,3-dimethylpiperidin-1-yl)-3-methyl-1-oxobutan-2-ylcarbamate (65 g, 148 mmol) and hydrogen chloride (4 M HCl in dioxane, 720 mL, 2880 mmol). Upon completion of addition, the reaction mixture was stirred at rt for 2.5 h. After this time, the reaction mixture was concentrated to yield a gel. The gel was co-evaporated with methanol (8×100 mL) and then CH$_2$Cl$_2$ (7×100 mL) to yield a solid (initially weighing 57 g, HCl salt).

Step 7: Phenyl (R)-1-((S)-4-(4-chlorophenyl)-4-hydroxy-3,3-dimethylpiperidin-1-yl)-3-methyl-1-oxobutan-2-ylcarbamate

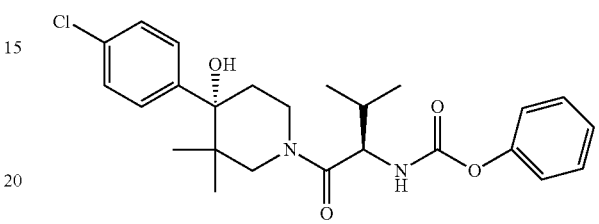

The carbamate synthesis was carried out in two separate flasks. The amounts disclosed herein are the totals used to carryout the experiments in the two flasks. (R)-2-amino-1-((S)-4-(4-chlorophenyl)-4-hydroxy-3,3-dimethylpiperidin-1-yl)-3-methylbutan-1-one, HCl. (20 g, 53.3 mmol) and DIPEA (18.61 mL, 107 mmol) were mixed in CH$_2$Cl$_2$ (15 mL) at rt with stirring, and then phenyl carbonochloridate (6.71 mL, 53.3 mmol) in 10 ml of methylene chloride was added drop wise via an addition funnel. Upon completion of addition, the reaction mixture was stirred for one hour. After this time, an additional 0.2 equiv. of DIPEA followed by a solution of phenyl chloroformate in methylene chloride was added. The organic and aqueous layers were separated. The organic layer was washed with 1N HCl, sat aq. NaHCO$_3$, and brine; dried and then stripped to give an oil. To the oil, with stirring at rt, was added 25 ml of MeCN. Upon completion of addition, solids formed after stirring for 10 min. Ether (50 mL) was added and the resulting mixture was stirred for 5 minutes. After this time, additional ether (25 mL) was added and stirring was continued for 15 minutes. At the conclusion of this period, the resulting solids were collected by filtration and then rinsed with ether to give 13 grams of the crude solid which was used without further purification. The filtrate was concentrated to yield a residue. The residue was purified over silica gel (9:1 to 3:1 to 1:1 hexanes/EtOAc to 100% EtOAc) to give an additional 6.72 g of product 6.72 g (total mass yield 19.7 g, 81% yield).

Step 8: Compound of Formula I

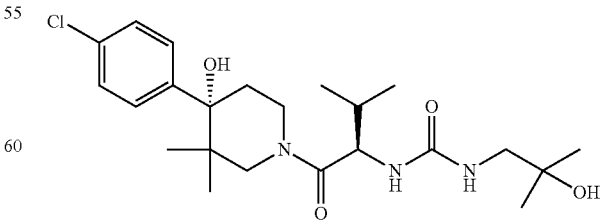

Under a nitrogen atmosphere, phenyl (R)-1-((S)-4-(4-chlorophenyl)-4-hydroxy-3,3-dimethylpiperidin-1-yl)-3-methyl-1-oxobutan-2-ylcarbamate (16.0 g, 34.9 mmol), 1-amino-2-methylpropan-2-ol (3.42 g, 38.3 mmol) and DIPEA (6.70 mL, 38.3 mmol) were mixed with stirring in MeCN (30 mL) at rt. The resulting suspension was heated to reflux, during which time the suspension became a colorless solution. After stirring at reflux for about 20 minutes, solids precipitated. After stirring at reflux for 1.5 h, 20 ml of acetonitrile and another 0.1 equiv. of 1-amino-2-methylpropan-2-ol and DIPEA were added. The reaction mixture was stirred for an additional 1.5 h. After this time, the reaction mixtured was removed from heating and allowed to cool to rt. While cooling to rt, water was added to precipitate the product (~240 mL) and the resulting free flowing suspension was stirred overnight. At the conclusion of this period, the resulting solids were collected by filtration, rinsed 2 times with water and then dried under high vacuum for 6 hours to give 15.4 grams of solids. These solids (and an additional ~1 gram of pilot batch) were slurried in 50 mL of acetone at rt with stirring, and then 3 times the volume of water (150 mL) was added. The free-flowing suspension was stirred overnight. After this time, the resulting solids were collected by filtration, rinsed twice with water and then dried for 48 h to give 15.2 grams of the Compound of Formula I as a solid. $^1$H NMR (500 MHz, methanol-d$_4$, rotameric) δ ppm 7.47 (dd, J=15.4, 8.8 Hz, 4 H), 7.31 (dd, J=8.5, 5.2 Hz, 4 H), 4.71 (dd, J=12.1, 6.1 Hz, 2 H), 4.54 (ddd, J=12.9, 2.5, 2.2 Hz, 1 H), 3.98-4.08 (m, 2 H), 3.58-3.68 (m, 2 H), 3.48 (dd, J=12.9, 1.4 Hz, 1 H), 3.13-3.21 (m, 2 H), 3.06-3.14 (m, 4 H), 2.70 (td, J=13.6, 4.7 Hz, 1 H), 2.61 (td, J=13.5, 5.0 Hz, 1 H), 2.09 (dq, J=13.2, 6.6 Hz, 1 H), 1.95 (dq, J=13.3, 6.7 Hz, 1 H), 1.60 (ddd, J=13.9, 2.5, 2.3 Hz, 1 H), 1.51 (ddd, J=14.2, 2.6, 2.5 Hz, 1 H), 1.16 (s, 6 H), 1.14 (d, J=1.7 Hz, 6 H), 1.05 (d, J=7.2 Hz, 3 H), 0.98 (d, J=7.2 Hz, 3 H), 0.94 (d, J=6.6 Hz, 3 H), 0.91 (d, J=6.6 Hz, 3 H), 0.82 (s, 3 H), 0.81 (s, 3 H), 0.79 (s, 3 H), 0.75 (s, 3 H). $^{13}$C NMR (126 MHz, methanol-d$_4$) δ ppm 173.6, 173.3, 161.1, 160.8, 144.8, 144.6, 133.82 (2 C, s), 130.2 (4 C, s), 128.3 (4 C, s), 76.0, 76.0, 71.7, 71.7, 55.9, 55.2, 55.1, 51.8 (2 C, s), 51.1, 43.0, 40.4, 39.9, 39.3, 34.8, 33.7, 33.1, 32.4, 27.2 (2 C, s), 27.1 (2 C, s), 23.1, 22.8, 21.4, 21.1, 20.3, 19.8, 17.9, 17.7, m/z: 454.2 [M+]$^+$.

Step 9:

EXAMPLE 1

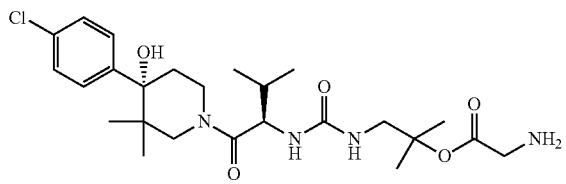 [SMILES: CC(C)[C@@H](NC(=O)NCC(C)(C)OC(=O)CN)C(=O)N1CC[C@](O)(c2ccc(Cl)cc2)C(C)(C)C1]

A solution of Compound 1 (200 mg, 0.441 mmol), 2-(((9H-fluoren-9-yl)methoxy)carbonylamino)acetic acid (262 mg, 0.881 mmol), and DMAP (10.76 mg, 0.088 mmol) was treated with DCC (182 mg, 0.881 mmol), and the mixture was stirred at room temperature for 7 hours. Analysis by LC/MS indicated only ~50% conversion of the starting material, and indicated a substantial amount of the anhydride resulting from self-coupling of the amino acid. The mixture was treated with additional 2-(((9H-fluoren-9-yl)methoxy)carbonylamino)acetic acid (262 mg, 0.881 mmol) and DCC (182 mg, 0.881 mmol), then stirred overnight at room temperature.

The mixture was filtered, and the filtrate was purified over a 24 g silica gel column, eluting at 40 mL/minute with an ethyl acetate/hexanes gradient to yield a film which contained some unidentified impurities. The material was re-purified over a 24 g silica gel column, eluting at 40 mL/minute with 4% then 10% methanol/methylene chloride to yield 1-(3-((R)-1-((S)-4-(4-chlorophenyl)-4-hydroxy-3,3-dimethylpiperidin-1-yl)-3-methyl-1-oxobutan-2-yl(ureido)-2-methylpropan-2-yl 2-(((9H-fluoren-9-yl)methoxy)carbonylamino)acetate (197 mg, 0.261 mmol, 59.2% yield) as a colorless film. MS (ES+)=733.3 (M+H)$^+$.

A solution of 1-(3-((R)-1-((S)-4-(4-chlorophenyl)-4-hydroxy-3,3-dimethylpiperidin-1-yl)-3-methyl-1-oxobutan-2-yl(ureido)-2-methylpropan-2-yl 2-(((9H-fluoren-9-yl)methoxy)carbonylamino)acetate (180 mg, 0.245 mmol) and 1-octanethiol (0.426 mL, 2.455 mmol) in anhydrous THF (3 mL) was treated with DBU (7.40 µL, 0.049 mmol), and the mixture was stirred overnight at room temperature.

The solvent was evaporated with a stream of nitrogen, and the residue was purified over a 12 g silica gel column, eluting at 30 mL/min with a methanol/methylene chloride gradient to yield 1-(3-((R)-1-((S)-4-(4-chlorophenyl)-4-hydroxy-3,3-dimethylpiperidin-1-yl)-3-methyl-1-oxobutan-2-yl)ureido)-2-methylpropan-2-yl 2-aminoacetate (105 mg, 0.205 mmol, 84% yield), as a colorless glass. MS (ES+)=511.1 (M+H)$^+$.

EXAMPLE 2

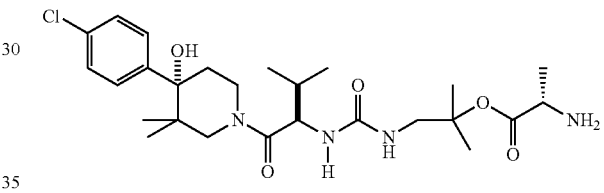

A solution of compound 1 (200 mg, 0.396 mmol), BOC-L-Alanine (188 mg, 0.991 mmol), 4-(Dimethylamino)pyridine (121 mg, 0.991 mmol) in DCM (5 mL) was treated with a solution N,N'-Dicyclohexylcarbodiimide (229 mg, 1.110 mmol) in DCM (2 mL) and the mixture stirred at rt for 24 h. The reaction was filtered to removed N,N-dicyclohexyl urea and the filtrate concentrated on a rotary evaporator. The residue was dissolved in EtOAc (15 mL), cooled to 0° C. and additional N,N-dicyclohexyl urea filtered off. The filtrate was washed with 1 M KHSO$_4$ (3 times), water and 5% NaHCO$_3$ (3 times), dried (Na$_2$SO$_4$) and concentrated. The crude product was purified by flash chromatography using a 12 g silica gel cartridge and eluting with 0-75% EtOAc/hexanes to give (S)-1-(3-((R)-1-((S)-4-(4-chlorophenyl)-4-hydroxy-3,3-dimethylpiperidin-1-yl)-3-methyl-1-oxobutan-2-yl)ureido)-2-methylpropan-2-yl 2-(tert-butoxycarbonylamino)propanoate (160 mg, 0.256 mmol, 64.5% yield) as a solid.

A solution of (S)-1-(3-((R)-1-((S)-4-(4-chlorophenyl)-4-hydroxy-3,3-dimethylpiperidin-1-yl)-3-methyl-1-oxobutan-2-yl)ureido)-2-methylpropan-2-yl 2-(tert-butoxycarbonylamino)propanoate (160 mg, 0.256 mmol) in DCM (0.5 mL) was treated with 4M Hydrochloric acid (4 mL, 16.00 mmol) in dioxane and stirred at rt.

After 10 min, LC-MS showed the starting was >95% consumed by-product derived from the cleavage of the piperidine amide bond (m/z=240) as also formed in approximately 10% yield. The reaction was added dropwise to saturated NaHCO$_3$ solution (35 mL) and the mixture extracted with DCM (3×50 mL). The extract was washed with brine, dried (Na2SO4) and the crude product purified by medium C18 chromatography (13 g cartridge) and eluting with 0-70% A/B.

Flow Rate: 30 mL/min
Mobile Phase: A: 10% MeOH-90% water-0.1% TFA
B: 90% MeOH-10% water-0.1% TFA The fraction containing the product were pooled, concentrated on a rotary evaporator to remove most of the methanol solvent, the residue treated with saturated NaHCO₃ solution to pH 8 and extracted with DCM. The extract was washed with brine, dried (Na₂SO₄) and concentrated on a rotary evaporator to give the product was a white semicrystalline solid. The solid was dissolved in acetonitrile/water (2 mL/8 mL) and the cloudy solution was frozen and lyophilized to give (S)-1-(3-((R)-1-((S)-4-(4-chlorophenyl)-4-hydroxy-3,3-dimethylpiperidin-1-yl)-3-methyl-1-oxobutan-2-yl)ureido)-2-methylpropan-2-yl 2-aminopropanoate (65 mg, 0.121 mmol, 47.4% yield) as a solid.

EXAMPLE 3

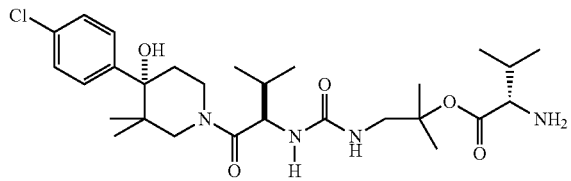 [SMILES: CC(C)[C@H](N)C(=O)OC(C)(C)CNC(=O)N[C@@H](C(=O)N1CC[C@](O)(c2ccc(Cl)cc2)C(C)(C)C1)C(C)C]

A solution of compound 1 (215 mg, 0.426 mmol), BOC-L-Valine (231 mg, 1.066 mmol) and 4-(Dimethylamino)pyridine (130 mg, 1.066 mmol) in DCM (5 mL) was treated with a solution of N,N'-Dicyclohexylcarbodiimide (246 mg, 1.193 mmol) in DCM (2 mL) and the mixture stirred at rt for 48 h. The reaction was filtered to removed N,N-dicyclohexyl urea and the filtrate concentrated on a rotary evaporator. The residue was dissolved in EtOAc (15 mL), cooled to 0° C. and additional N,N-dicyclohexyl urea filtered off. The filtrated was washed with 1 M KHSO₄ (3 times), water and 5% NaHCO₃ (3 times), dried (Na₂SO₄) and concentrated. The crude product was purified by flash chromatography using a 12 g silica gel cartridge and eluting 0-75% EtOAc/hexanes to give the desired product (S)-1-(3-((R)-1-((S)-4-(4-chlorophenyl)-4-hydroxy-3,3-dimethylpiperidin-1-yl)-3-methyl-1-oxobutan-2-yl)ureido)-2-methylpropan-2-yl 2-(tert-butoxycarbonylamino)-3-methylbutanoate (170 mg, 0.260 mmol, 61.1% yield) as a solid.

A solution of (S)-1-(3-((R)-1-((S)-4-(4-chlorophenyl)-4-hydroxy-3,3-dimethylpiperidin-1-yl)-3-methyl-1-oxobutan-2-yl)ureido)-2-methylpropan-2-yl 2-(tert-butoxycarbonylamino)-3-methylbutanoate (170 mg, 0.260 mmol) in DCM (0.5 mL) was treated with 4 M Hydrochloric acid (4 mL, 16.00 mmol) in dioxane and stirred at rt. After 10 min, LC-MS showed the starting material was >95% consumed.

The reaction was added dropwise to saturated NaHCO₃ solution (35 mL) and the mixture extracted with DCM (3×50 mL). The extract was washed with brine, dried (Na₂SO₄) and the crude product purified by medium C18 chromatography (13 g cartridge) and eluting with 0-70% A/B.
Flow Rate: 30 mL/min
Mobile Phase: A: 10% MeOH-90% water-0.1% TFA
B: 90% MeOH-10% water-0.1% TFA The fraction containing the product were pooled, concentrated on a rotary evaporator to remove most of the methanol solvent, the residue treated with saturated NaHCO₃ solution to pH 8 and extracted with DCM. The extract was washed with brine, dried (Na₂SO₄) and concentrated on a rotary evaporator to give the product as a semicrystalline solid. The solid was dissolved in acetonitrile/water (2 mL/8 mL) and the cloudy solution was frozen and lyophilized to give (S)-1-(3-((R)-1-((S)-4-(4-chlorophenyl)-4-hydroxy-3,3-dimethylpiperidin-1-yl)-3-methyl-1-oxobutan-2-yl)ureido)-2-methylpropan-2-yl 2-amino-3-methylbutanoate (55 mg, 0.097 mmol, 37.4% yield) as a solid.

EXAMPLE 4

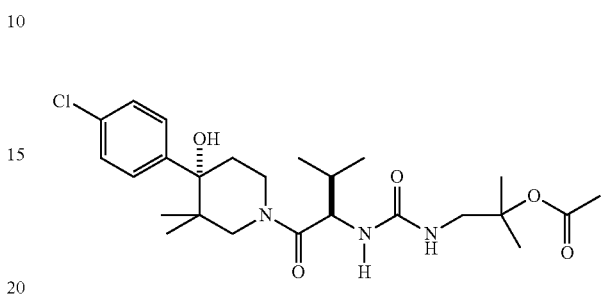

A solution of compound 1 (100 mg, 0.220 mmol), DCM (10 mL), Acetic anhydride (0.104 mL, 1.101 mmol), triethylamine (0.061 mL, 0.441 mmol) and 4-dimethylaminopyridine (5.38 mg, 0.044 mmol) was stirred in a stoppered flask for 48 h. LCMS showed the desired product with 20% starting material remaining. The mixture was diluted with DCM (25 mL), washed with pH 4 acetate buffer (5 mL) and brine, dried (Na₂SO₄) and concentrated on a rotary evaporator. The crude product was purified by flash chromatography using a 12 g silica gel cartridge and eluting with 0-100% EtOAC/hexanes (TLC visualization by cerium molyb.). The fraction containing the product were pooled and concentrated on a rotary evaporator to give a solid. The solid was dissolved in 10% aqueous acetonitrile and lyophilized to give 1-(3-((R)-1-((S)-4-(4-chlorophenyl)-4-hydroxy-3,3-dimethylpiperidin-1-yl)-3-methyl-1-oxobutan-2-yl)ureido)-2-methylpropan-2-yl acetate (65 mg, 0.128 mmol, 58.3% yield) as an amorphous solid.

EXAMPLE 5

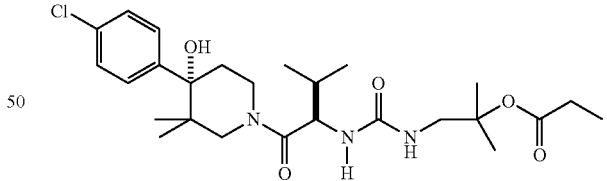

A solution of compound 1 (100 mg, 0.220 mmol), propionic anhydride (0.282 mL, 2.203 mmol), DMAP (53.8 mg, 0.441 mmol) and DCM (5 mL) was stirred at rt for 24 h and then concentrated on a rotary evaporator. The crude product was purified by medium pressure C18 chromatography using a 13 g ISCO cartridge and eluting with 0-80% gradient MeOH/H₂O over 10 min. The fractions containing the product were pooled, concentrated and lyophilized to give 1-(3-((R)-1-((S)-4-(4-chlorophenyl)-4-hydroxy-3,3-dimethylpiperidin-1-yl)-3-methyl-1-oxobutan-2-yl)ureido)-2-methylpropan-2-yl propionate (90 mg, 0.173 mmol, 79% yield) as a solid.

EXAMPLE 6

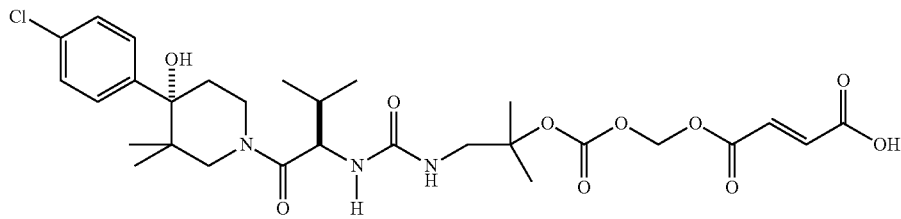 [SMILES: CC(C)[C@@H](NC(=O)NCC(C)(C)OC(=O)OCOC(=O)/C=C/C(=O)O)C(=O)N1CC[C@](O)(c2ccc(Cl)cc2)C(C)(C)C1]

Compound 1 (0.215 g, 0.474 mmol) in DCM (3 mL) is added pyridine (0.192 mL, 2.368 mmol) followed by dropwise addition of chloromethyl carbonochloridate (0.084 mL, 0.947 mmol) over a period of 3 min at RT. The initial heterogeneous mixture becomes homogenous towards the end of the addition of chloromethyl carbonochloridate. The contents were stirred at RT for 1 h at which time LCMS (Luna 3u C18 4.6×30 mm; solvent A=10% MeOH, 90% H2O, 0.1% TFA, solvent B=90% MeOH, 10% H2O, 0.1% TFA) indicated the presence of a major peak with the desired mass. The reaction mixture was concentrated, the residue dissolved in MeOH (1.5 mL) and subjected to prep. HPLC (Phenomenex Luna AXIA 5u C18 30×100 mm; 8 min. gradient; solvent A=10% MeOH, 90% H2O, 0.1% TFA, solvent B=90% MeOH, 10% H2O, 0.1% TFA). The desired fractions are collected, concentrated and partitioned between DCM (10 mL) and brine (10 mL). The DCM layer is separated, dried over sodium sulfate and concentrated to yield chloromethyl 1-(3-((R)-1-((S)-4-(4-chlorophenyl)-4-hydroxy-3,3-dimethylpiperidin-1-yl)-3-methyl-1-oxobutan-2-yl)ureido)-2-methylpropan-2-yl carbonate (0.19 g, 0.348 mmol, 73.4% yield).

To chloromethyl 1-(3-((R)-1-((S)-4-(4-chlorophenyl)-4-hydroxy-3,3-dimethylpiperidin-1-yl)-3-methyl-1-oxobutan-2-yl)ureido)-2-methylpropan-2-yl carbonate (0.19 g, 0.348 mmol) in DMF (2 mL) are sequentially added triethylamine (0.048 mL, 0.348 mmol) and fumaric acid (0.020 g, 0.174 mmol) at RT. Contents heated at 70° C. (oil bath temp.) for 20 h. The reaction mixture was cooled to rt and subjected to prep. HPLC (Phenomex Luna AXIA 30×100 mm; 10 min. gradient; solvent A=10% CH3CN, 90% H2O, 0.1% TFA, solvent B=90% CH3CN, 10% H2O, 0.1% TFA). The desired fractions are collected and concentrated. The residue is partitioned between DCM (20 mL) and brine (10 mL). The DCM layer is dried over sodium sulfate and concentrated to yield (R,E)-3-((S)-4-(4-chlorophenyl)-4-hydroxy-3,3-dimethylpiperidine-1-carbonyl)-2,8,8-trimethyl-5,10,14-trioxo-9,11,13-trioxa-4,6-diazaheptadec-15-en-17-oic acid (0.022 g, 0.035 mmol, 10.11% yield).

The semi-solid that is obtained is dissolved in MeOH (0.2 mL) and water (1.5 mL) and freeze dried overnight to a solid. Anal. RP-HPLC: $t_R$=3.40 min (YMC S5 Combi ODS 4.6×50 mm; 4 min. gradient; solvent A=10% MeOH, 90% H2O, 0.2% H3PO4, solvent B=90% MeOH, 10% H2O, 0.2% H3PO4. Purity: >96%. MS (ESI) m/z 626.20 (M+H)+

EXAMPLE 7

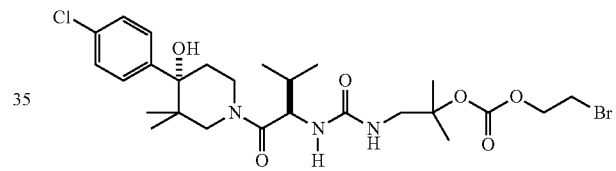

Step 1:
Compound 1 in CH2Cl2 (12 mL) at 0° C. was added pyridine (0.534 mL, 6.61 mmol) followed by 2-bromoethyl carbonochloridate (413 mg, 1.982 mmol). The reaction was allowed to warm to rt slowly and stir for 4 h. The reaction was concentrated and partitioned between EA (40 mL) and water (20 mL). The layers were separated and the EA layer was further washed with 0.5 N HCl, dilute aq. NaHCO3, then brine. The EA layer was dried (Na2SO4), filtered and concentrated. The product was purified via flash chromatography on SiO2 (25% to 50% EA/heptane to 100% EA) and dried to afford 2-bromoethyl 1-(3-((R)-1-((S)-4-(4-chlorophenyl)-4-hydroxy-3,3-dimethylpiperidin-1-yl)-3-methyl-1-oxobutan-2-yl)ureido)-2-methylpropan-2-yl carbonate (790 mg, 1.267 mmol, 96% yield) as a solid.

HPLC Purity: 97%, rt 4.00 min; LCMS: 606.3 (M+)

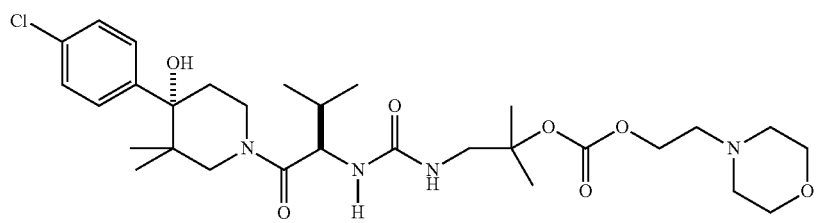 [SMILES: CC(C)[C@@H](NC(=O)NCC(C)(C)OC(=O)OCCN1CCOCC1)C(=O)N1CC[C@](O)(c2ccc(Cl)cc2)C(C)(C)C1]

Step 2;

To a solution of 2-bromoethyl 1-(3-((R)-1-((S)-4-(4-chlorophenyl)-4-hydroxy-3,3-dimethylpiperidin-1-yl)-3-methyl-1-oxobutan-2-yl)ureido)-2-methylpropan-2-yl carbonate (780 mg, 1.289 mmol) and K$_2$CO$_3$ (356 mg, 2.58 mmol) in DMF (3 mL) was added morpholine and the reaction was stirred at rt overnight. After drying the crude product overnight under high vacuum, the residual glass was purified via column chromatography (50% EA/hep to 100% EA to 5% MeOH/EA) to furnish 1-(3-((R)-1-((S)-4-(4-chlorophenyl)-4-hydroxy-3,3-dimethylpiperidin-1-yl)-3-methyl-1-oxobutan-2-yl)ureido)-2-methylpropan-2-yl 2-morpholinoethyl carbonate (620 mg, 1.014 mmol, 79% yield) as a foam. $^1$H NMR (CDCl$_3$, 400 MHz, rotameric) δ 7.40-7.24 (m, 4H), 5.44 (dd, J=21.9, 8.8 Hz, 1H), 5.13 (dt, J=21.1, 5.7 Hz, 1H), 4.82 (m, 1H), 4.65 (br d, 0.5H), 4.20 (t, J=6.2 Hz, 2H), 3.95 (m, 0.5H), 3.71 (t, J=4.8 Hz, 4H), 3.58 (m, 1H), 3.43 (m, 3H), 3.15 (dt, J=13.1, 2.6 Hz, 0.5H), 3.05 (d, J=12.7 Hz, 0.5H), 2.64 (t, J=5.7 Hz, 2H), 2.51 (t, J=4.4 Hz, 4H), 1.96 (m, 1H), 1.54 (m, 1H), 1.47-1.43 (m, 6H), 1.06 (d, J=6.6 Hz, 1.5H), 0.97-0.76 (m, 10.5H). HPLC Purity: >99%, rt 3.23 min (Chromalith Speedrod, C18, 4.6×50 mm, 10% MeOH/water to 90% MeOH/water with 0.2% H$_3$PO$_4$, 4 min gradient, 4 mL/min) LCMS: 611.38 (M+)

Hydrochloride Salt Formation:

To a solution of 1-(3-((R)-1-((S)-4-(4-chlorophenyl)-4-hydroxy-3,3-dimethylpiperidin-1-yl)-3-methyl-1-oxobutan-2-yl)ureido)-2-methylpropan-2-yl 2-morpholinoethyl carbonate (222 mg, 0.363 mmol) in EA (4 mL) was added HCl in dioxane (0.086 mL, 0.345 mmol). The mixture was sonicated briefly until a slight haze forms in the solution then allow to stir rapidly overnight. The solids were filtered and dried to provide 220 mg of a solid. $^1$H NMR (DMSO-d$_6$, 400 MHz, rotameric) δ 7.45 (m, 2H), 7.35 (m, 2H), 6.44 (m, 0.5H, 6.20 (m, 0.5H), 5.09 (s, 0.7H), 4.58 (m, 0.7H), 4.39 (m, 2H), 3.94 (M, 4H), 3.73 (t, J=11.9 Hz, 2H), 3.43-2.89 (m, 18H), 1.52-1.32 (m, 8H), 0.2 (d, J=6.6 Hz, 1H), 0.82 (d, J=6.6 Hz, 3H), 0.79 (d, J=6.6 Hz, 2H), 0.69 (m, 3H), 0.61 (m, 4H). HPLC Purity: >99%, rt 3.25 min (Chromalith Speedrod, C18, 4.6× 50 mm, 10% MeOH/water to 90% MeOH/water with 0.2% H$_3$PO$_4$, 4 min gradient, 4 mL/min)

EXAMPLE 8

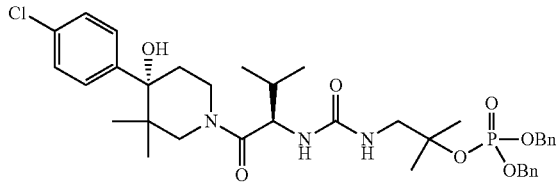 [SMILES: CC(C)[C@@H](NC(=O)NCC(C)(C)OP(=O)(OCc1ccccc1)OCc1ccccc1)C(=O)N1CC[C@](O)(c2ccc(Cl)cc2)C(C)(C)C1]

1-((R)-1-((S)-4-(4-chlorophenyl)-4-hydroxy-3,3-dimethylpiperidin-1-yl)-3-methyl-1-oxobutan-2-yl)-3-(2-hydroxy-2-methylpropyl)urea (Compound 1, 300 mg, 0.661 mmol) was dissolved in CH$_2$Cl$_2$ (10 mL) at 25° C. with stirring under nitrogen then dibenzyl diisopropylphosphoramidite (456 mg, 1.322 mmol) was added followed by 1H-tetrazole (93 mg, 1.322 mmol). The reaction contained some solids which dissolved after several minutes. H$_2$O$_2$ (0.020 mL, 0.661 mmol) was added and stirred for several hours. The reaction was then washed with 10% Na$_2$S$_2$O$_5$, 1N HCl, and brine. The organic layer was dried over sodium sulfate and concentrated to give 560 mg of a glass which was purified over silica gel in 3:1 to 1:1 hexanes/EtOAc to 100% EtOAc to 9:1 methylene chloride/methanol to give dibenzyl 1-(3-((R)-1-((S)-4-(4-chlorophenyl)-4-hydroxy-3,3-dimethylpiperidin-1-yl)-3-methyl-1-oxobutan-2-yl)ureido)-2-methylpropan-2-yl phosphate (460 mg, 0.644 mmol, 97% yield) of a glass as product.

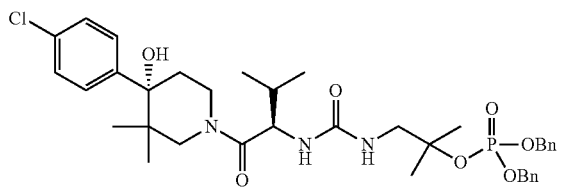 [SMILES: CC(C)[C@@H](NC(=O)NCC(C)(C)OP(=O)(OCc1ccccc1)OCc1ccccc1)C(=O)N1CC[C@](O)(c2ccc(Cl)cc2)C(C)(C)C1]

Utility

In general, the prodrugs of the compound of formula (I) have been shown to be modulators of chemokine receptor activity. By displaying activity as a modulator of chemokine receptor activity, the compounds are expected to be useful in the treatment of human diseases associated with chemokines and their cognate receptors.

The prodrugs of the invention were prepared to provide improved solubility and stability properties over Compound I, as shown below in Table I. The solubility of Compound 1 is 0.047 mg/mL in pH 6.6 buffer as determined by the methods outlined above. The chemical stability half-life at pH 1 is 30 h and at pH 7.4 it is >22 h according to the methods outlined in the above assays. For Table 1, the aqueous stability half-life refers to the conversion of the prodrug to compound 1.

TABLE 1

| Ex. # | Prodrug Structure | Aq. sol., mg/mL (pH) | Aq. Stability half-life (pH 1/7.4) Hrs |
|---|---|---|---|
| 1 | Cl-phenyl-piperidine-valine-urea-CH$_2$C(CH$_3$)$_2$-O-C(O)-CH$_2$-NH$_2$ structure | 1.1 (6.5) | 159/86 |

TABLE 1-continued

| Ex. # | Prodrug Structure | Aq. sol., mg/mL (pH) | Aq. Stability half-life (pH 1/7.4) Hrs |
|---|---|---|---|
| 2 | | Not tested | Not tested |
| 3 | | >0.6 (6.5) | 237/>22 |
| 4 | | 0.03 (6.5) | 29/>22 |
| 5 | | 0.04 (6.5) | 25 ? >22 |
| 6 | | 2.2 (6.5) | 61/49 |
| 7 | | 0.34 (6.5) | 85/131 |

TABLE 1-continued

| Ex. # | Prodrug Structure | Aq. sol., mg/mL (pH) | Aq. Stability half-life (pH 1/7.4) Hrs |
|---|---|---|---|
| 8 | (structure) | >7.2 (7.4) | 32/ |
| 9 | (structure) | 1.6 (6.5) | 25/72 |
| 10 | (structure) | Not tested | <1/ |
| 11 | (structure) | Not tested | 107/0.3 |
| 12 | (structure) | | 82/0.3 |
| 13 | (structure) | Not determined | 10.1/0.25 |
| 14 | (structure) | 0.18 (7.4) | 49/107 |

TABLE 1-continued

| Ex. # | Prodrug Structure | Aq. sol., mg/mL (pH) | Aq. Stability half-life (pH 1/7.4) Hrs |
|---|---|---|---|
| 15 | (structure) | 0.022 (7.4) | >22/>22 |
| 16 | (structure) | Not determined | unstable |
| 17 | (structure) | <0.007 (7.4) | >22/>22 |
| 18 | (structure) | 0.059 (7.4) | >22/>22 |
| 19 | (structure) | 0.08 (6.5) | >22/>22 |
| 20 | (structure) | 0.317 (6.5) | >22/>22 |

TABLE 1-continued

| Ex. # | Prodrug Structure | Aq. sol., mg/mL (pH) | Aq. Stability half-life (pH 1/7.4) Hrs |
|---|---|---|---|
| 21 | | >16 (7.4) | >22/>22 |
| 22 | | >7 (6.5) | 44/>22 |
| 23 | | >0.3 (6.5) | 25/23 |
| 24 | | 1.1 (6.5) | 77/>22 |
| 25 | | >0.32 (7.4) | 16.6/73 |
| 26 | | Not tested | Not tested |

TABLE 1-continued

| Ex. # | Prodrug Structure | Aq. sol., mg/mL (pH) | Aq. Stability half-life (pH 1/7.4) Hrs |
|---|---|---|---|
| 27 | | 0.5 (6.5) | 36/>22 |
| 28 | | 7.1 (6.5) | 1.4/>22 |
| 29 | | 4.8 (6.5) | 81/>22 |
| 30 | | 0.31 (6.5) | 33/>22 h |
| 31 | | >3.3 (6.5) | 61/>22 |
| 32 | | 1.12 (6.5) | >22/>22 |

TABLE 1-continued

| Ex. # | Prodrug Structure | Aq. sol., mg/mL (pH) | Aq. Stability half-life (pH 1/7.4) Hrs |
|---|---|---|---|
| 33 | 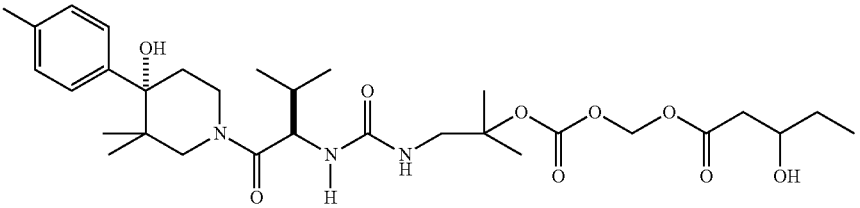 | >1.6 (6.5) | >22/>22 |
| 34 | 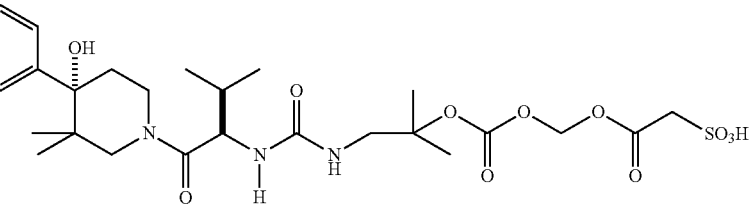 | >0.18 (6.5) | 47/>22 |
| 35 | 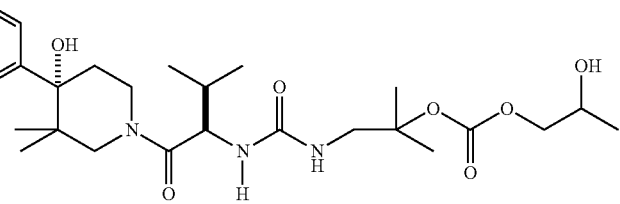 | 0.18 (6.5) | 100/30.3 |
| 36 | 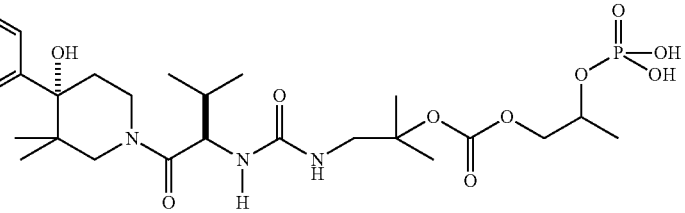 | >1.2 (6.5) | 97/>22 h |

Thermodynamic Equilibrium Aqueous Solubility Assay

Standards Preparation

The calibration standard is prepared by accurately weighing 0.5-0.7 mg of sample in 5 ml of methanol. If the material is not fully soluble in methanol, other solvents such as DMSO or mixed solvents will be used.

*The calibration standard is typically prepared fresh immediately before the start of the assay. A two-point calibration curve should be used to determine the concentration of the final solution. A serial dilution is performed on the standard solution.

Test Sample Preparation

The final saturated solution is prepared by adding 1.0 ml of the appropriate aqueous solvent to the remaining portion of material (~1 mg/1 ml) into a 1 dram vial. The solution is sonicated and vortexed for ~30 seconds. The sample solution is placed on an orbiter that continually agitates the sample solutions for 15-24 hours at room temperature. The final saturated solution is then transferred to a 1.5 ml Eppendorf tube and centrifuged for ~2 min. at 10000 rpms. The supernatant from the saturated solution is transferred to a glass HPLC vial without filtering since the 1.5 mL volume is insufficient to saturate a syringe filter. This sample preparation procedure nullifies the effects of non-specific binding to the filtering apparatus.

LC Quantitation:

The standards and sample are analyzed by HPLC using either UV/Vis diode array or variable wavelength detection. Typical quantitation wavelengths are 210 or 254 nm; detection wavelength can be individually customized to optimize sensitivity. In addition to UV detection, mass spectrometry detection is recommended if available in order to confirm the identity of the HPLC-UV peak of interest.

Dilutions of aqueous test solutions are performed if HPLC-UV peak is beyond the linear portion of the standard calibration curve. Typical dilutions include 100 ul/900 ul (×10) or 500 ul/500 ul (2×), as required.

Reagents

HPLC grade solvents are employed.

Solution Stability Assay

Acetonitrile Stock Solution: Prepare an Acetonitrile Stock Solution of the prodrug by dissolving 1.5-2.0 mg of accurately weighted compound in 5.0 mL of acetonitrile in 5 mL volumetric flask.

pH 7.4 Buffer Working Solution: Prepare a pH 7.4 Buffer working Solution of drug by adding 1.5 mL of the Acetonitrile Stock Solution to 3.5 mL of stability buffer in a 20 mL scintillation vial, mix very well. Using a 3 mL syringe withdraw ~3 mL of solution and filter using the Gelman 0.45 μm syringe filter into a clean 1.5 mL LC vial. This filtered solution will be used to evaluate the prodrug degradation throughout the course of the study. Target concentration: 90-120 μg/mL (70% Aqueous: 30% Acetonitrile)

pH 1.0 Acidic Working Solution: Prepare a pH1.0 Working Solution of drug by adding 1.5 mL of the Acetonitrile Stock Solution to 3.5 mL of stability buffer in a 20 mL scintillation vial, mix very well. Using a 3 mL syringe withdraw ~3 mL of solution and filter using the Gelman 0.45 μm syringe filter into a clean 1.5 mL LC vial. This filtered solution will be used to evaluate the prodrug degradation throughout the course of the study. Target concentration: 90-120 μg/mL (70% Aqueous: 30% Acetonitrile)

Following the sample preparation procedure described above a single sample (n=1) is prepared for each pH condition. The samples were then placed in an HPLC autosampler maintained at 37° C. and samples were analyzed over a 24 hr period. Prodrug remaining (%) is reported relative to the initial peak area (t=0 h). In cases where a conversion to parent half-life could be calculated, a t1/2 was generated. Confirmation of the conversion to parent from the prodrug was obtained by LCMS and HPLC analysis of the final timepoint samples.

Typical LC parameters are shown below:
HPLC System: HP1100 Series, Hewlett Packard., Heated autosampler
Analytical column. Synergi 4u Hydro C18, 4.6 mm×5.0 cm, Phenomenex
Column temperature: 40° C.
Autosampler temp: 37° C.
Flow rate: 1.0 mL/min
Injection Volume: 10 μL
Mobile Phase: A: Acetonitrile
   B: 0.1% Phosphoric acid in water
Run Time: 14.0 minutes
Typical LCMS parameters are shown below:
LC-MS System: Surveyor HPLC system, ThermoFinnigan LCQ Deca XP Max (Ion trap)
Analytical column. Synergi 4u Hydro C18, 4.6 mm×5.0 cm, Phenomenex
Column temperature: 40° C.
Autosampler temp: 22° C.
Flow rate: 1.0 mL/min
Injection Volume: 5 ΞL
Mobile Phase: A: 95% Acetonitrile/5% 20 mM Ammonium Acetate
   B: 5% Acetonitrile/95% 20 mM Ammonium Acetate
LCQ Parameters
Sheath Flow Rate: 81.64
Aux/Sweep Flow Rate: 19.01
Current (uA): 10.89
Voltage (kV): 5.00
Capillary©: 348.10
Capillary Voltage (V): 30.44

Mammalian chemokine receptors provide a target for interfering with or promoting immune cell function in a mammal, such as a human. Compounds that inhibit or promote chemokine receptor function are particularly useful for modulating immune cell function for therapeutic purposes.

Accordingly, the present invention is directed to one or more prodrugs of the compound of formula (I) which are believed to be useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, the instant compounds which inhibit one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, the instant compounds which promote one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for the instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematological malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., *Toxocara*), eosinophilic gastroenteritis (e.g., *Anisakis* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of one or more prodrugs of the compound of formula (I) in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, the compounds according to the present invention could be used to test their effectiveness. Specifically, such compounds may be provided in a commercial kit, for example, for use in pharmaceutical research involving the aforementioned diseases. The compounds of the instant invention is also useful for the evaluation of putative specific modulators of the chemokine receptors. In addition, one could utilize the compounds of this invention to examine the specificity of G protein coupled receptors that are not thought to be chemokine receptors, either by serving as examples of compounds which do not bind or as structural variants of compounds active on these receptors which may help define specific sites of interaction.

The prodrugs of the compound of formula (I) are used to treat or prevent disorders selected from rheumatoid arthritis, osteoarthritis, septic shock, atherosclerosis, aneurysm, fever, cardiovascular effects, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes mellitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, glomerulonephritis, and systemic lupus erythematosus.

In another aspect, the prodrugs of the compound of formula (I) are used to treat or prevent inflammatory disorders selected from rheumatoid arthritis, osteoarthritis, atherosclerosis, aneurysm, fever, cardiovascular effects, Crohn's disease, inflammatory bowel diseases, psoriasis, congestive heart failure, multiple sclerosis, autoimmune diseases, skin inflammatory diseases.

In another aspect, the prodrugs of the compound are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, the compounds of the invention may be used in combination with other drugs that are used in the treatment/prevention/suppression or amelioration of the diseases or conditions for which the compounds of the invention are useful. Such other drugs may be administered, by a route and in an amount commonly used therefore, contemporaneously or sequentially with a compound of the present invention. When the compounds of the invention are used contemporaneously with one or more other drugs, a pharmaceutical composition containing such other drugs in addition to the compounds of the invention may be used. Accordingly, the pharmaceutical compositions of the present invention include those that also contain one or more other active ingredients, in addition to the compounds of the invention.

Examples of other active ingredients that may be combined with the compounds of the invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal anti-inflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors; (j) cholesterol lowering agents such as HMG-COA reductase inhibitors (lovastatin, simvastatin and pravastatin, fluvastatin, atorvastatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone and pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (n) other compound such as 5-aminosalicylic acid and prodrugs thereof, anti-metabolites such as azathioprine and 6-mercaptopurine, and cytotoxic cancer chemotherapeutic agents. The weight ratio of the compounds of the invention to the second active ingredient may be varied and will depend upon the effective doses of each ingredient.

Generally, an effective dose of each will be used. Thus, for example, when the compounds of the invention are combined with an NSAID the weight ratio of the compound of the present invention to the NSAID will generally range from about 1000:1 to about 1:1000, or alternatively from about 200:1 to about 1:200. Combinations of the compounds of the invention and other active ingredients will generally also be within the aforementioned range, but in each case, an effective dose of each active ingredient should be used.

The compounds are administered to a mammal in a therapeutically effective amount. By "therapeutically effective amount" it is meant an amount of the compound that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. It can be administered alone, but generally will be administered with a pharmaceutical carrier selected on the basis of the chosen route of administration and standard pharmaceutical practice.

The dosage regimen for the compounds of the invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion. The compounds of this invention may be administered in a single daily dose, or the total daily dosage may be administered in divided doses of two, three, or four times daily.

The compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compounds of the invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compounds of the invention, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compounds of the invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

While the invention has been described in detail and with reference to specific embodiments thereof, it will be apparent to one skilled in the art that various changes and modifications can be made therein without departing from the spirit and scope thereof.

What is claimed is:

1. A compound of the formula

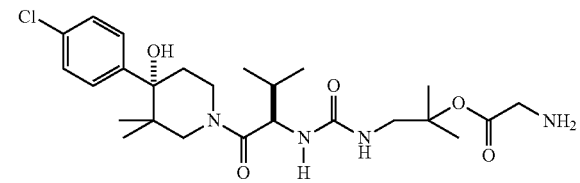

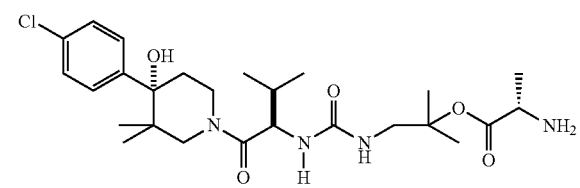

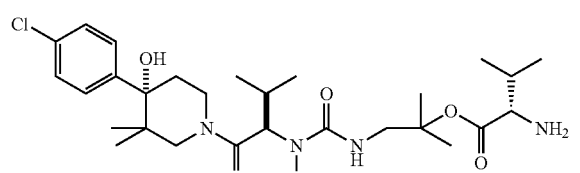

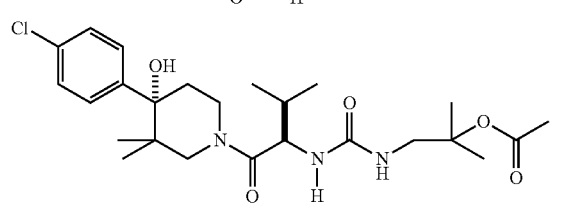

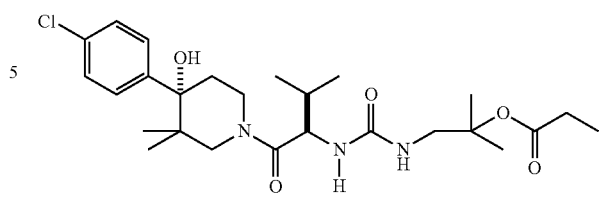

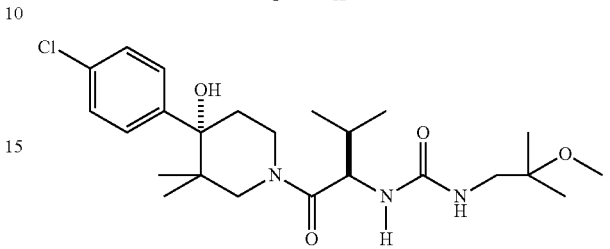

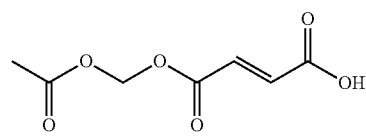

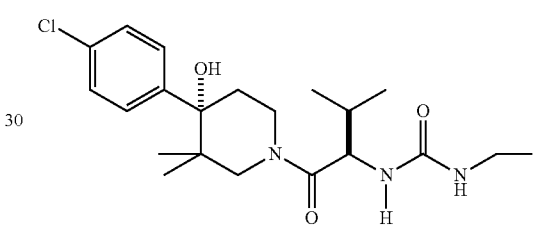

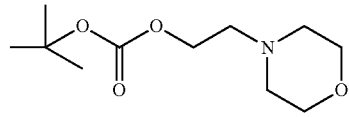

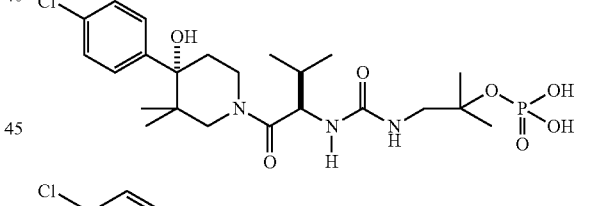

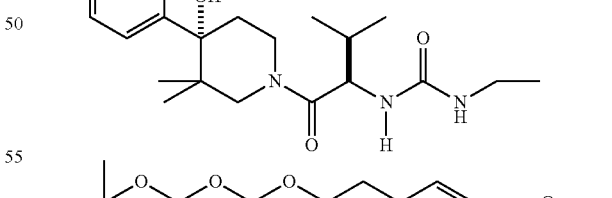

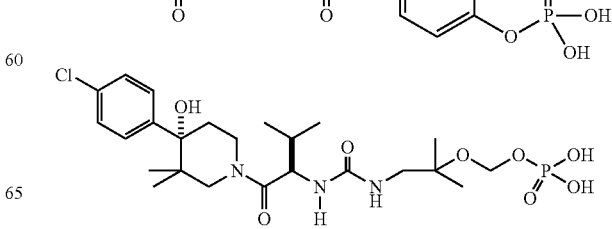

75
-continued
76
-continued
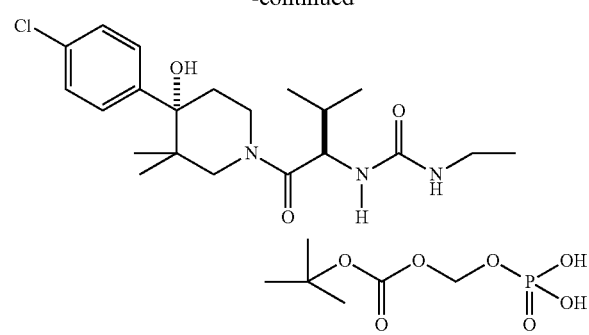
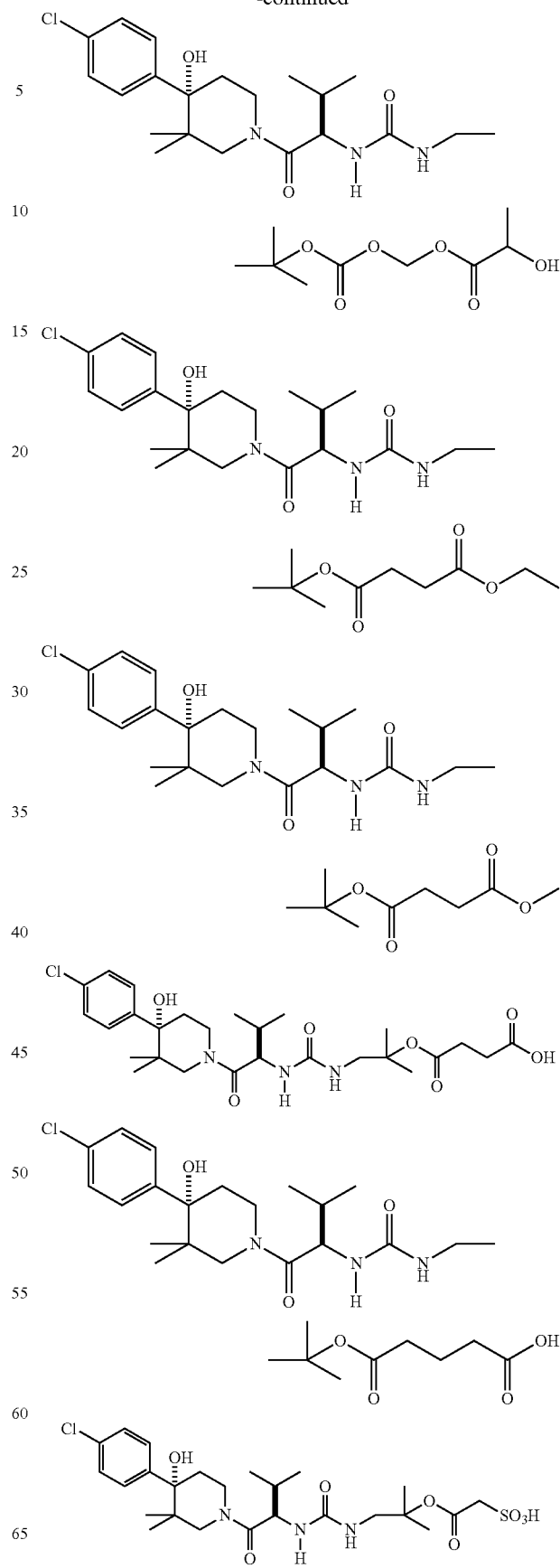

77
-continued
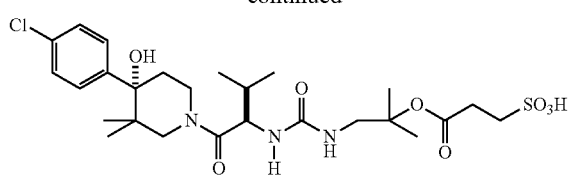
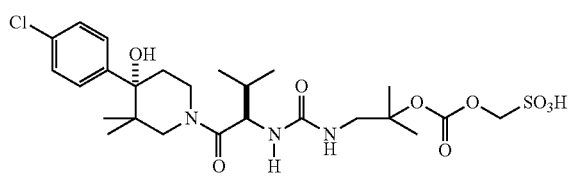
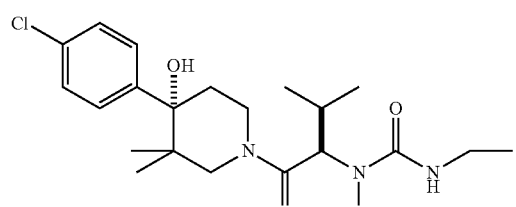
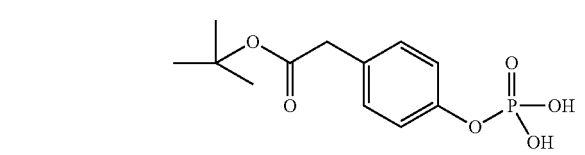
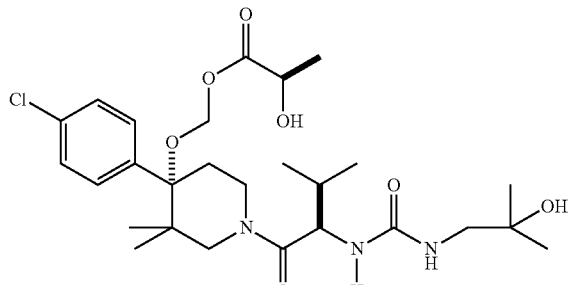
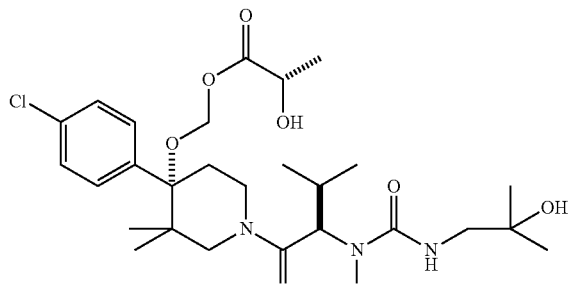
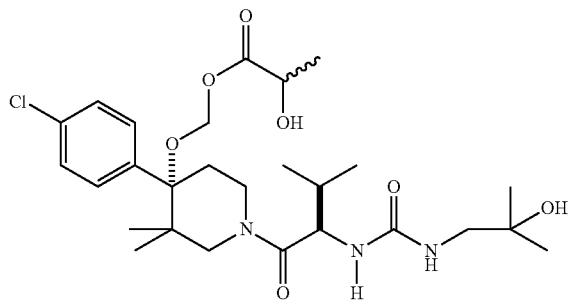
78
-continued
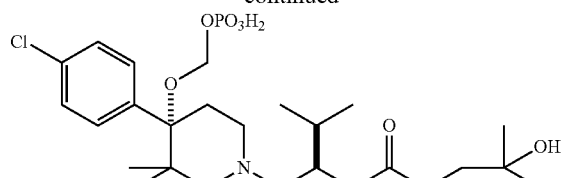
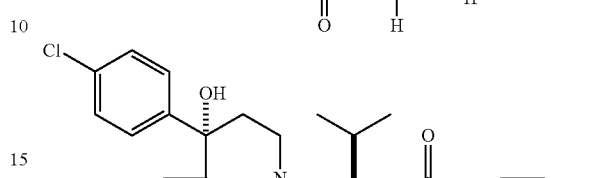
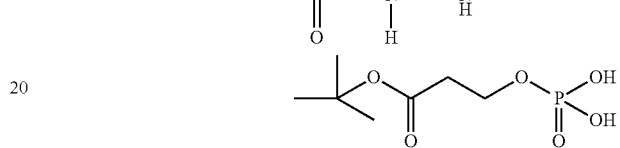
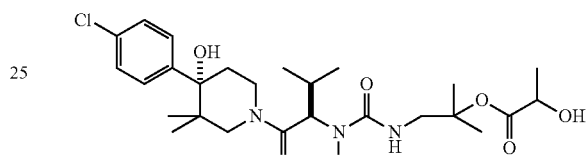
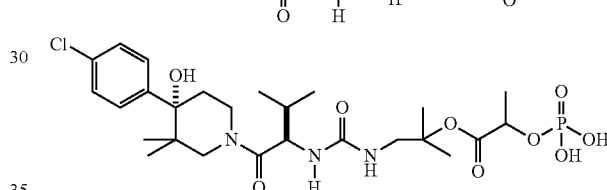
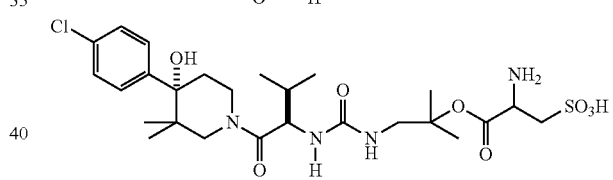
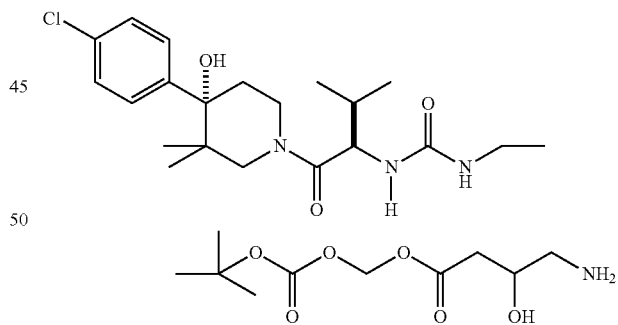
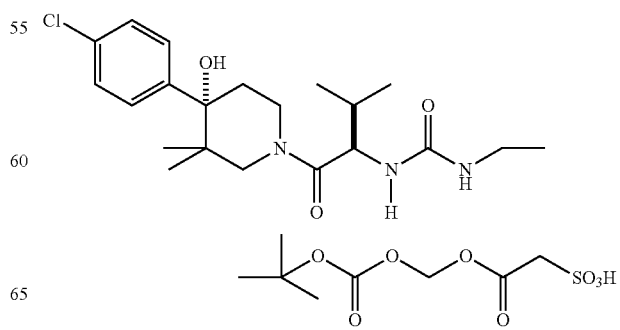

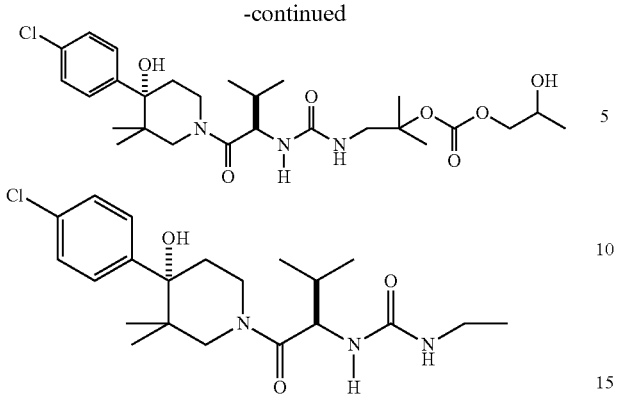
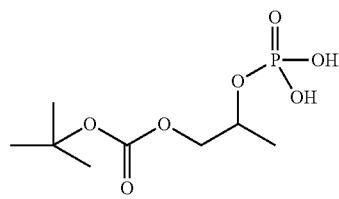
or a pharmaceutically acceptable salt form thereof.
2. A compound of the formula
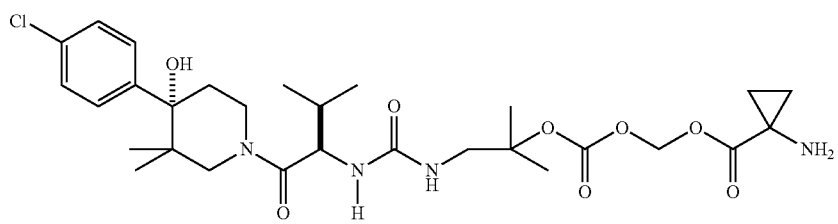 [SMILES: CC(C)[C@@H](NC(=O)NCC(C)(C)OC(=O)OCOC(=O)C1(N)CC1)C(=O)N1CC[C@](O)(c2ccc(Cl)cc2)C(C)(C)C1]
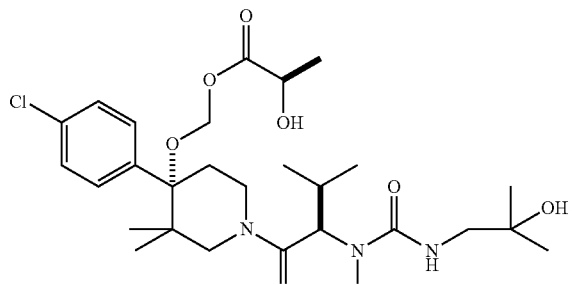
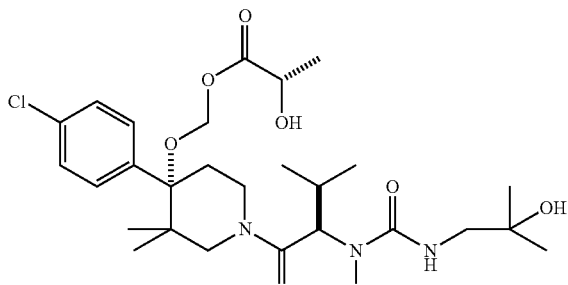
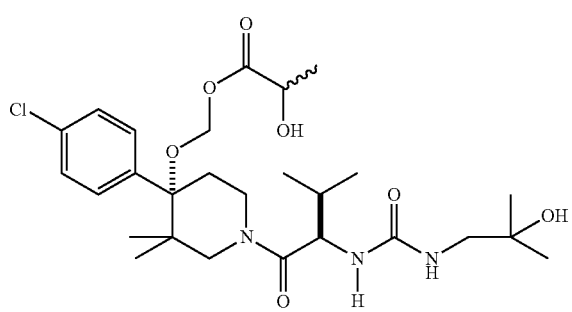 [SMILES: CC(O)C(=O)OCO[C@]1(c2ccc(Cl)cc2)CCN(C(=O)[C@H](NC(=O)NCC(C)(C)O)C(C)C)CC1(C)C]
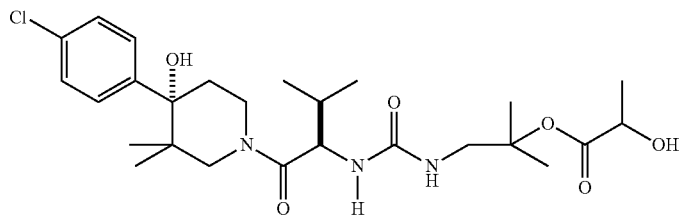 [SMILES: CC(O)C(=O)OC(C)(C)CNC(=O)N[C@@H](C(=O)N1CC[C@](O)(c2ccc(Cl)cc2)C(C)(C)C1)C(C)C]
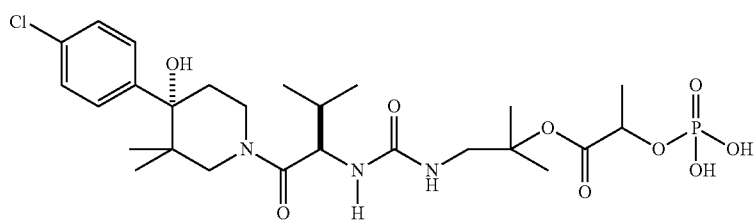 [SMILES: CC(OP(=O)(O)O)C(=O)OC(C)(C)CNC(=O)N[C@@H](C(=O)N1CC[C@](O)(c2ccc(Cl)cc2)C(C)(C)C1)C(C)C]

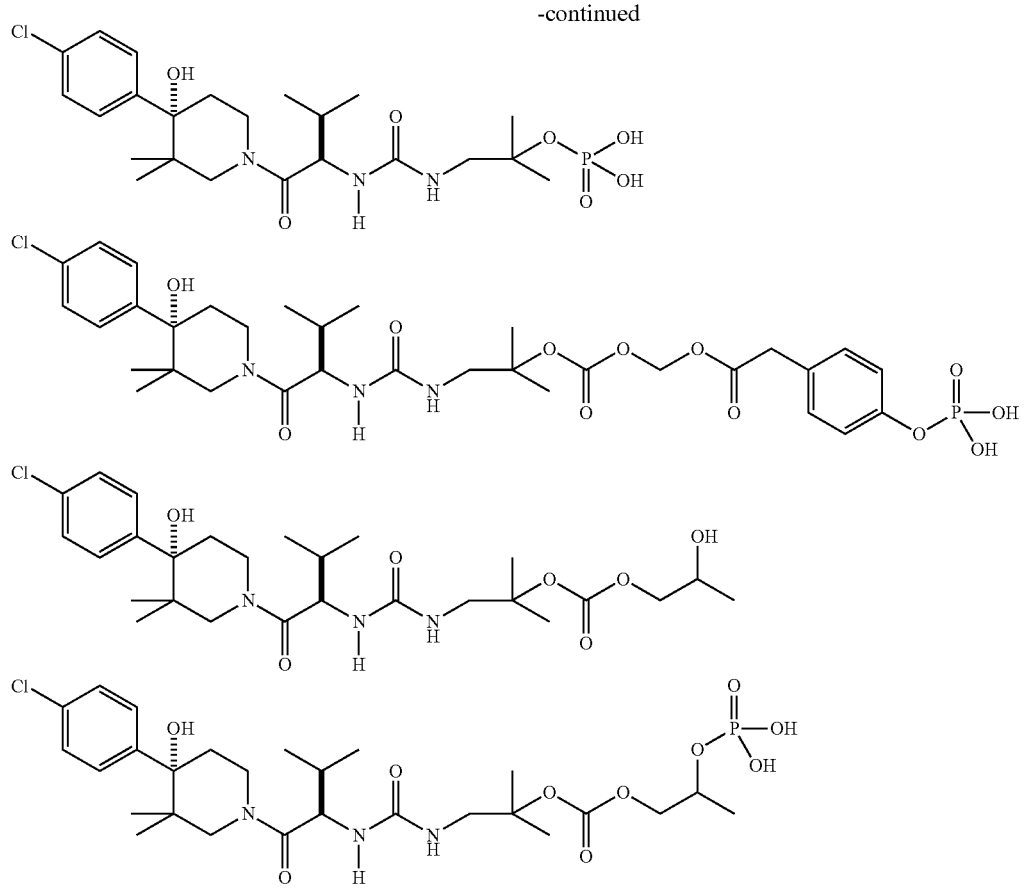

or a pharmaceutically acceptable salt form thereof.

3. A pharmaceutical composition comprised of a pharmaceutically acceptable carrier and a therapeutically effective amount of one or more of the compounds of claim 1.

4. A pharmaceutical composition comprised of a pharmaceutically acceptable carrier and a therapeutically effective amount of one or more of the compounds of claim 2.

* * * * *

UNITED STATES PATENT AND TRADEMARK OFFICE
CERTIFICATE OF CORRECTION

Page 1 of 8

PATENT NO.         : 8,410,139 B2
APPLICATION NO.    : 12/896955
DATED              : April 2, 2013
INVENTOR(S)        : John Hynes et al.

It is certified that error appears in the above-identified patent and that said Letters Patent is hereby corrected as shown below:

In the Claims:

Claim 1:

Columns 73, lines 38 to 66, Columns 74 to 78, all lines, Column 79, lines 2 to 15, and Column 80, lines 3 to 10, delete all structures and replace with the following structures:

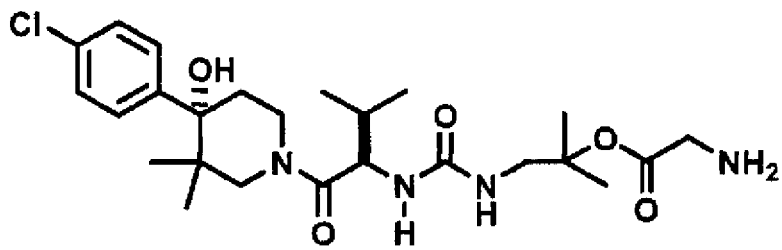

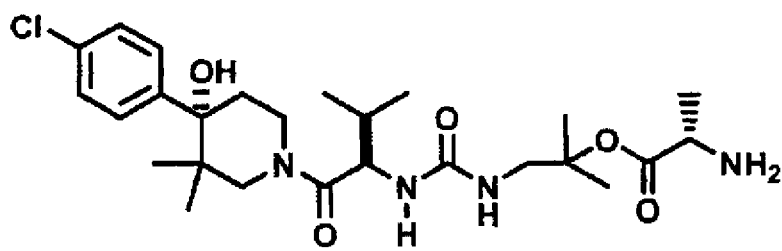

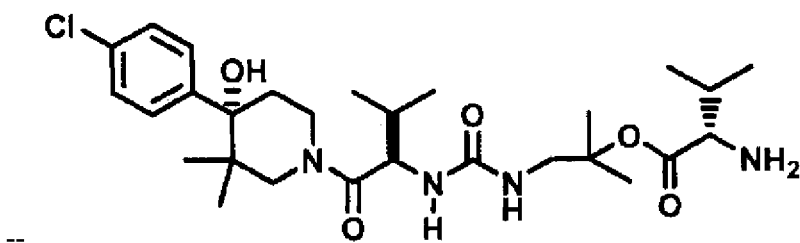

--

In the Claims:

Signed and Sealed this
Seventeenth Day of March, 2015

Michelle K. Lee
*Director of the United States Patent and Trademark Office*

CERTIFICATE OF CORRECTION (continued)
U.S. Pat. No. 8,410,139 B2

Claim 1 (continued):

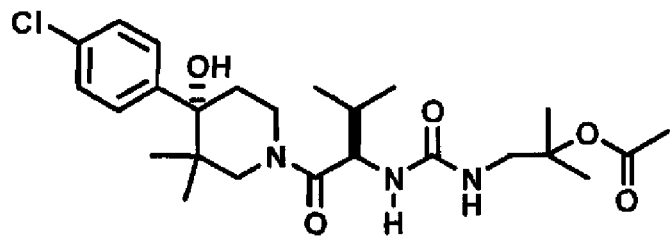

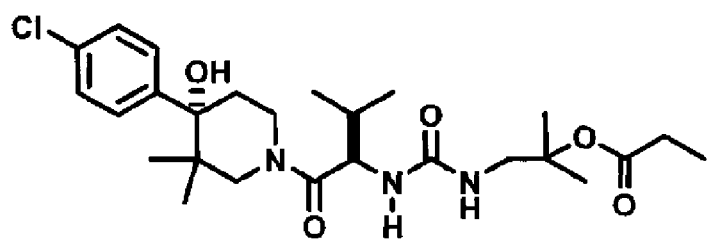

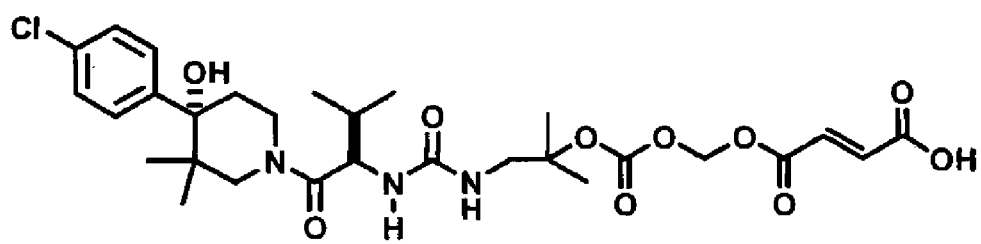

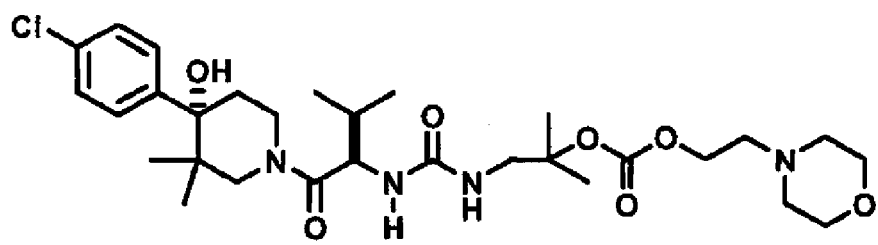

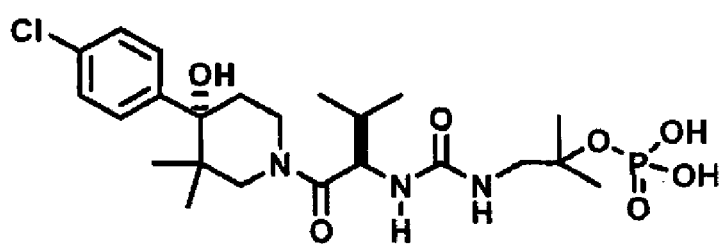

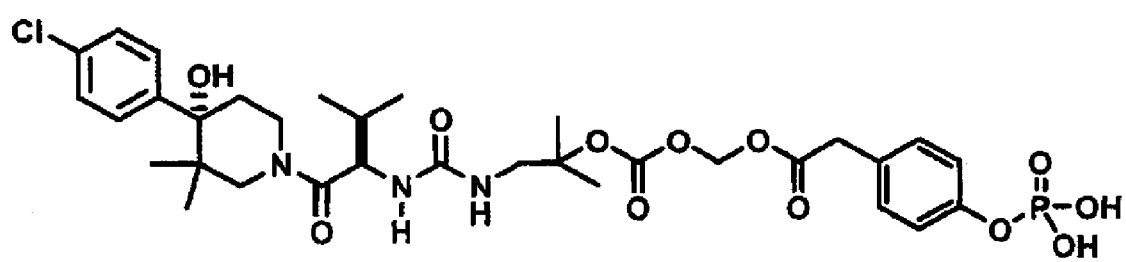

In the Claims:

Claim 1 (continued):
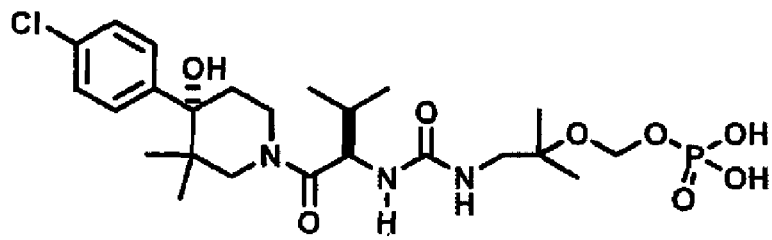
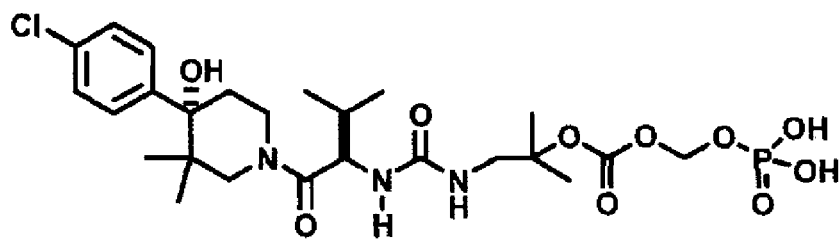
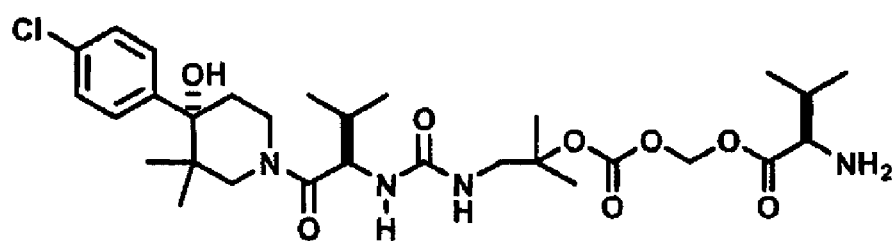
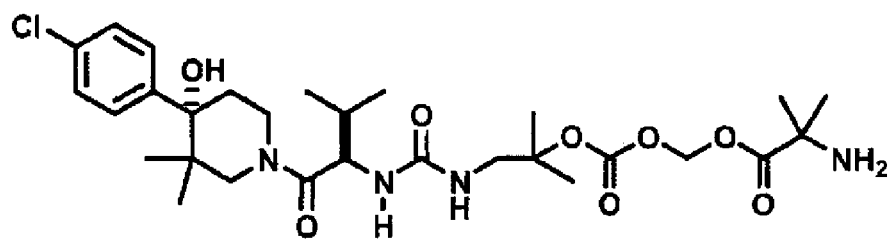
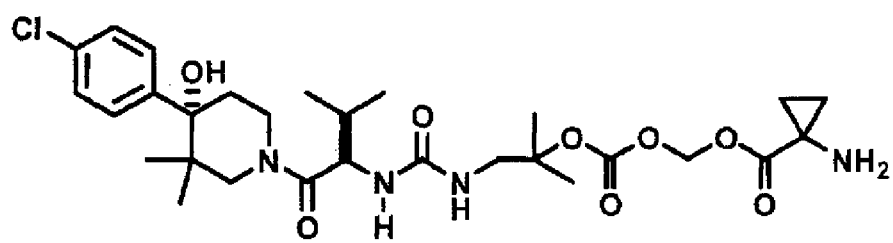
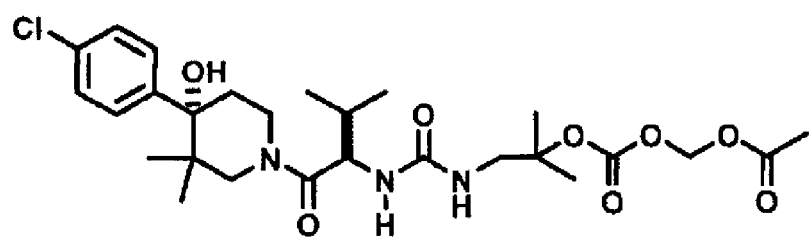
In the Claims:

Claim 1 (continued):
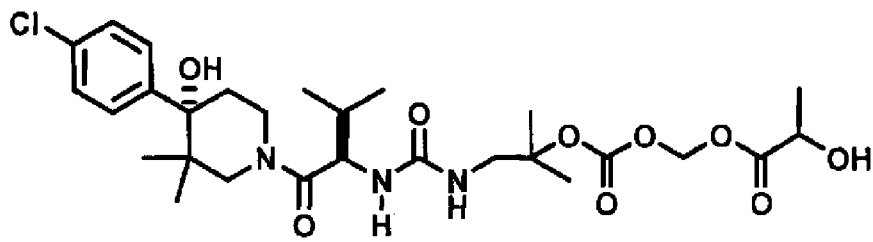
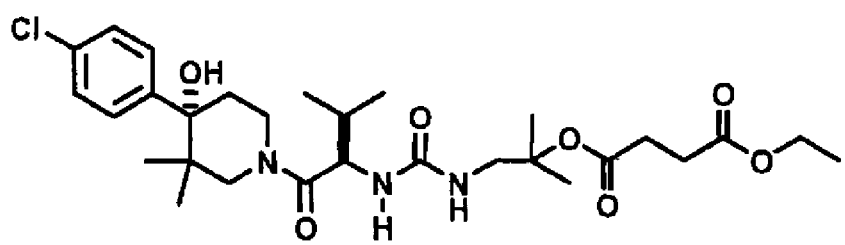
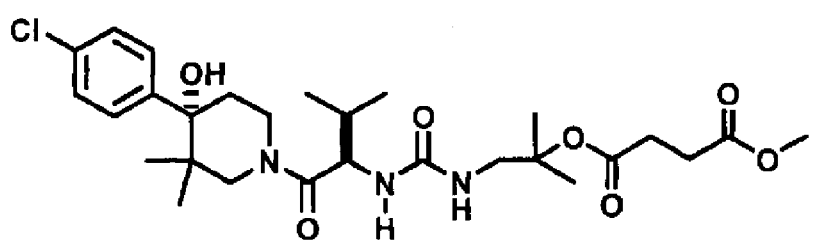
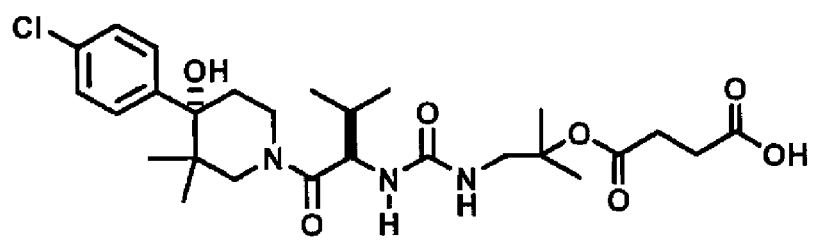
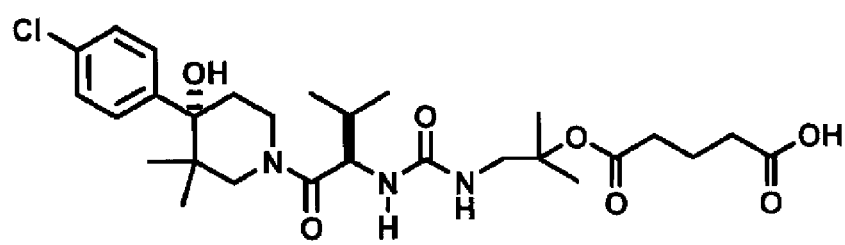
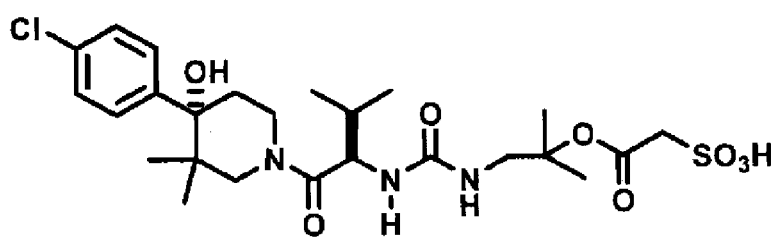
In the Claims:

Claim 1 (continued):
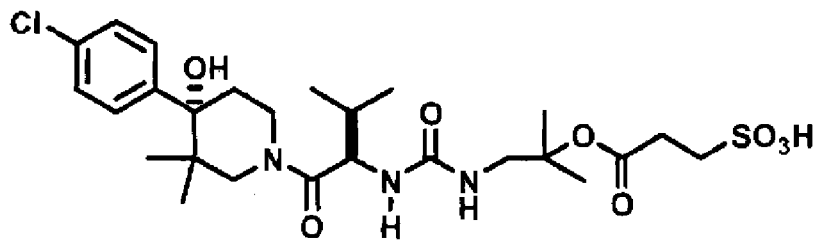
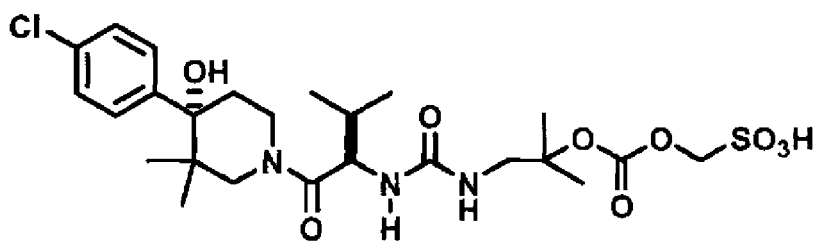
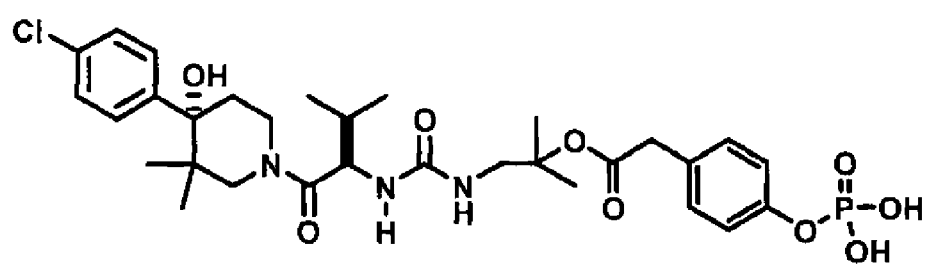
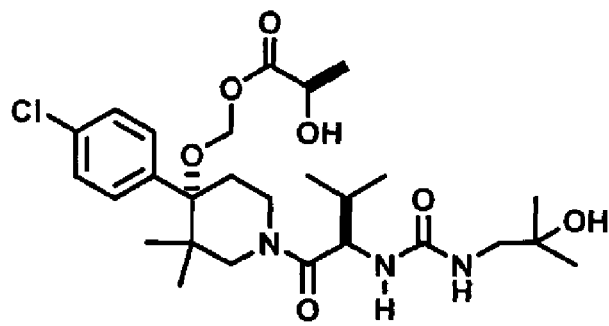
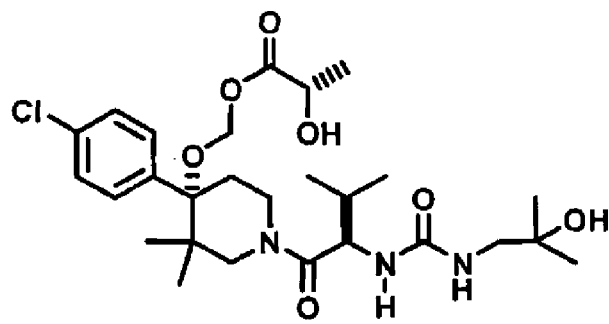
In the Claims:

Claim 1 (continued):
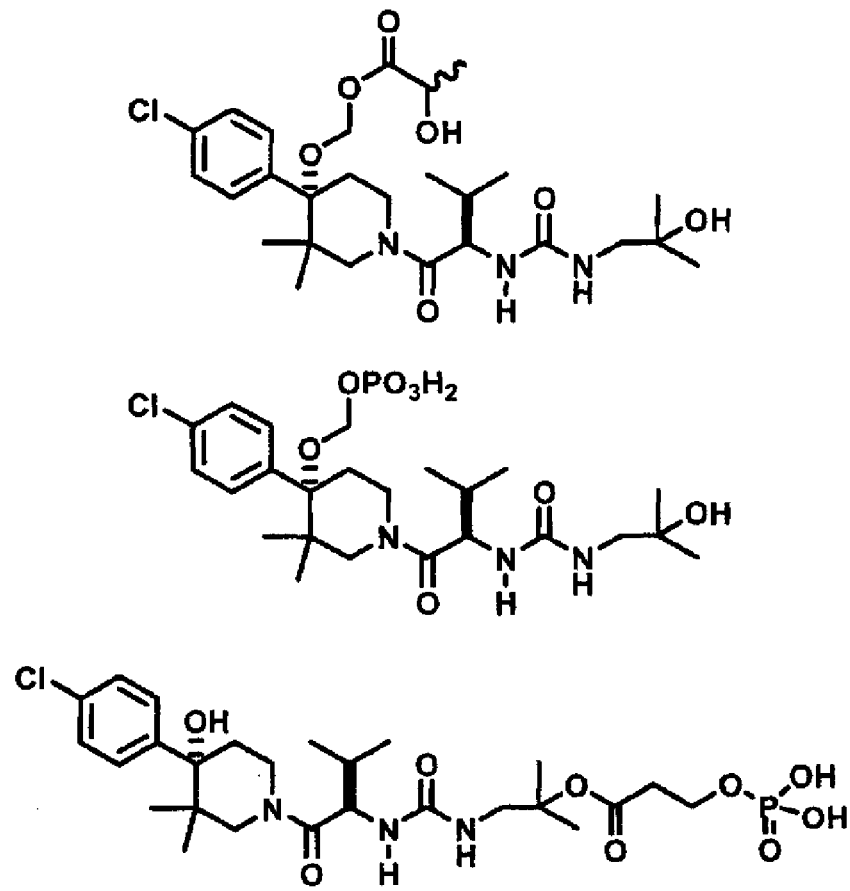
In the Claims:

CERTIFICATE OF CORRECTION (continued)
U.S. Pat. No. 8,410,139 B2

Claim 1 (continued):

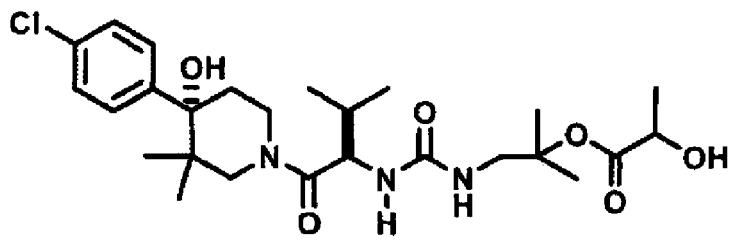

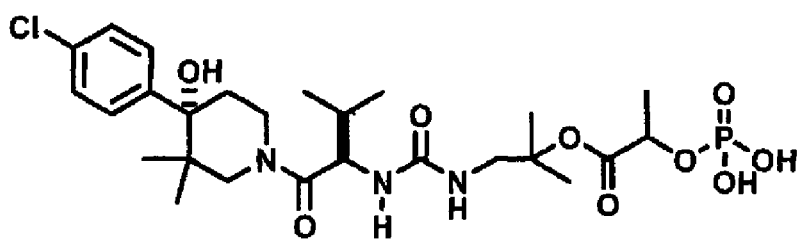

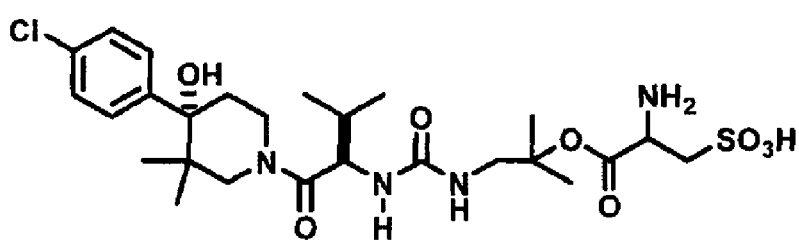

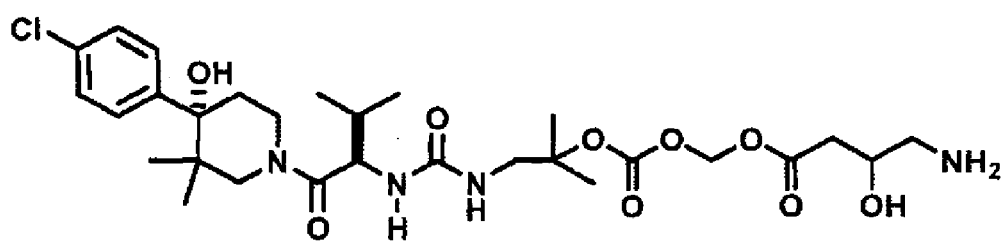

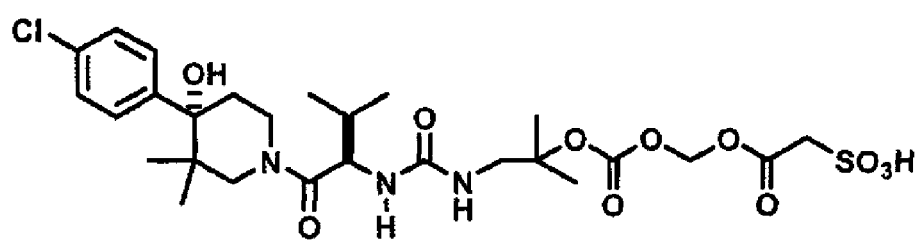

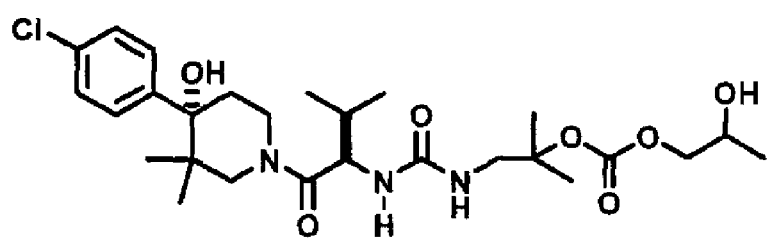

In the Claims:

Claim 1 (continued):
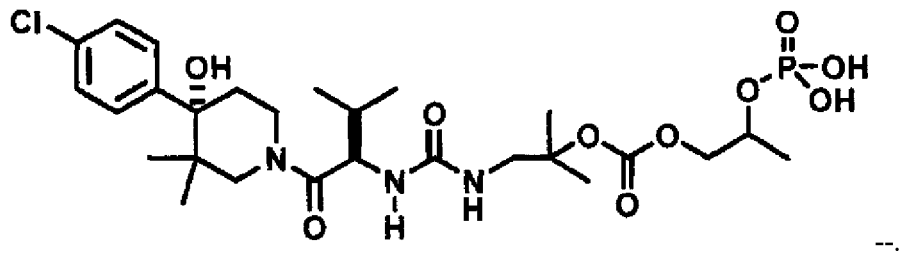
Column 80, line 13, move "or a pharmaceutically acceptable salt form thereof." after the second structure in Column 79.
Claim 2:
Column 80, line 17, move "2. A compound of the formula" before the third structure in Column 79.
Column 80, lines 27 to 38, move -- 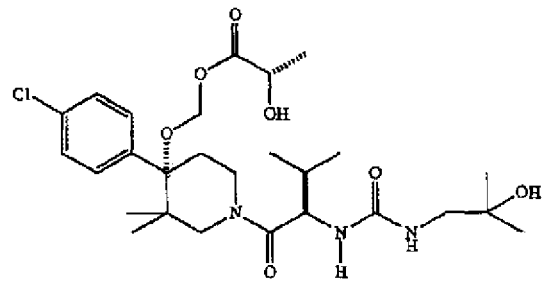 -- before the fifth structure in Column 79.